United States Patent
Romano

(10) Patent No.: US 6,758,822 B2
(45) Date of Patent: Jul. 6, 2004

(54) METHOD AND APPARATUS FOR MEASURING CARDIAC OUTPUT

(76) Inventor: Salvatore Romano, Via Boita, 33, I-50144 Firenze (IT)

(*) Notice: Subject to any disclaimer, the term of this patent is extended or adjusted under 35 U.S.C. 154(b) by 0 days.

(21) Appl. No.: 09/947,308

(22) Filed: Sep. 5, 2001

(65) Prior Publication Data

US 2002/0022785 A1 Feb. 21, 2002

Related U.S. Application Data

(63) Continuation-in-part of application No. PCT/EP00/03697, filed on Apr. 26, 2000.

(30) Foreign Application Priority Data

Apr. 27, 1999 (IT) .......................................... FI99A0098

(51) Int. Cl.[7] ................................................ A61B 5/02
(52) U.S. Cl. ........................ 600/526; 600/485; 600/481
(58) Field of Search ................................ 600/526, 508, 600/481, 483, 485, 486, 513

(56) References Cited

U.S. PATENT DOCUMENTS

| | | |
|---|---|---|
| 4,429,701 A | 2/1984 | Goor et al. |
| 4,595,015 A | 6/1986 | Jansen et al. |
| 4,798,211 A | 1/1989 | Goor et al. |
| 5,101,828 A | 4/1992 | Welkowitz et al. |
| 5,183,051 A | 2/1993 | Kraidin et al. |
| 5,199,438 A | 4/1993 | Pearlman |
| 5,211,177 A | 5/1993 | Chesney et al. |
| 5,241,966 A | 9/1993 | Finkelstein et al. |
| 5,265,011 A | 11/1993 | O'Rourke |
| 5,265,615 A | 11/1993 | Frank et al. |

(List continued on next page.)

FOREIGN PATENT DOCUMENTS

| | | |
|---|---|---|
| EP | 0 393 228 A1 | 10/1990 |
| EP | 0 448 979 A1 | 10/1991 |
| EP | 0 642 760 A1 | 3/1995 |
| EP | 0 569 506 B1 | 10/1995 |
| EP | 0 564 492 B1 | 10/1999 |
| EP | 0 947 160 A1 | 10/1999 |
| EP | 0 947 941 A2 | 10/1999 |
| WO | 90/03145 | 4/1990 |
| WO | 90/11042 | 10/1990 |
| WO | 92/06633 | 4/1992 |
| WO | 92/11804 | 7/1992 |
| WO | 92/12669 | 8/1992 |
| WO | 94/14372 | 7/1994 |
| WO | 94/22363 | 10/1994 |
| WO | 95/16391 | 6/1995 |
| WO | 97/24982 | 7/1997 |
| WO | 98/19594 | 5/1998 |
| WO | 99/02086 | 1/1999 |
| WO | 00/64339 | 11/2000 |

Primary Examiner—Max F. Hindenburg
Assistant Examiner—Navin Natnithithadha
(74) Attorney, Agent, or Firm—Young & Thompson

(57) ABSTRACT

Cardiac stroke volume and output are estimated using an arterial pressure signal, which may be obtained either invasively, using a catheter-mounted pressure sensor, or non-invasively, with an external plethysmographic sensor mounted with a finger cuff. Both pulsatile and non-pulsatile (continuous) components of the sensed pressure signal are analyzed. Stroke volume is estimated as a function of the ratio between the area under the entire pressure curve and a linear combination of various components of impedance. Depending on the embodiment, first and/or second time derivatives of the pressure signal are used to determine the impedance components. The estimated stroke volume is preferably corrected based on the amount of deviation from a reference pressure of the mean pressure, which itself is determined from the sensed pressure signal. The invention is thus able to estimate stroke volume and cardiac output from the pressure signal alone, with no need for calibration using other highly invasive techniques.

32 Claims, 23 Drawing Sheets

U.S. PATENT DOCUMENTS

| | | |
|---|---|---|
| 5,316,004 A | 5/1994 | Chesney et al. |
| 5,400,793 A | 3/1995 | Wesseling |
| 5,423,323 A | 6/1995 | Orth |
| 5,526,817 A | 6/1996 | Pfeiffer et al. |
| 5,533,511 A | 7/1996 | Kaspari et al. |
| 5,535,753 A | 7/1996 | Petrucelli et al. |
| 5,634,467 A | 6/1997 | Nevo |
| 5,647,369 A | 7/1997 | Petrucelli et al. |
| 5,730,138 A | 3/1998 | Wang |
| 5,746,698 A | 5/1998 | Bos et al. |
| 5,797,395 A | 8/1998 | Martin |
| 5,830,131 A | 11/1998 | Caro et al. |
| 5,865,758 A | 2/1999 | Louzianine |
| 5,876,347 A | 3/1999 | Chesney et al. |
| 5,913,826 A | 6/1999 | Blank |
| 6,004,274 A | 12/1999 | Nolan et al. |
| 6,010,457 A | 1/2000 | O'Rourke |
| 6,017,313 A | 1/2000 | Bratteli et al. |
| 6,048,318 A | 4/2000 | Chesney et al. |
| 6,071,244 A * | 6/2000 | Band et al. .................. 600/526 |
| 6,090,047 A | 7/2000 | Kass et al. |
| 6,117,087 A | 9/2000 | Kamm et al. |
| 6,165,130 A | 12/2000 | Chio |
| 6,224,585 B1 | 5/2001 | Pfeiffer |
| 6,228,033 B1 | 5/2001 | Kööbi et al. |
| 6,231,498 B1 | 5/2001 | Pfeiffer et al. |
| 6,270,461 B1 | 8/2001 | Chio |
| 6,290,651 B1 | 9/2001 | Chesney et al. |
| 6,315,735 B1 | 11/2001 | Joeken et al. |
| 6,348,038 B1 | 2/2002 | Band et al. |
| 6,394,958 B1 | 5/2002 | Bratteli et al. |

* cited by examiner

METHOD AND APPARATUS FOR MEASURING CARDIAC OUTPUT

CROSS-REFERENCE TO RELATED APPLICATIONS

This application is a Continuation-in-Part of International Patent Application No. PCT/EP00/03697, filed Apr. 26, 2000, which claims priority from Italian Patent Application No. FI99A000098, filed Apr. 27, 1999, of both of which the present application claims priority.

FIELD OF THE INVENTION

This invention relates to a method for determining the stroke volume and, hence, the cardiac output of a patient, as well as to a system that implements the method.

BACKGROUND ART

Accurate measurement of the cardiac output (CO) of a patient has proven to be a valuable diagnostic tool. Accordingly, several methods for determining CO have been developed, of which thermodilution, the direct oxygen Fick method, and the pulse contour method (PCM) are at present the most prevalent. These known methods for measuring CO, however, are affected by several drawbacks that greatly limit their application in the clinical setting as well as for purposes of research.

Measurement of CO using thermodilution, which is described, for example in Ganz, W. and Swan, H. J. C. (1972), "Measurement of blood flow by thermodilution," Am. J. Cardiol. 29, pp. 241–246, has become routine in the hemodynamic evaluation and management of critically ill patients. As is well known, this method is based on the law of conservation of energy and on the application of the Stewart-Hamilton equation, for which a number of conditions must be fulfilled. These conditions include complete mixing of the thermal indicator with blood, no loss of indicator within the dilution volume, and constant blood flow during the dilution time.

Inaccuracy in the determination of CO may result from the inconsistency of these assumptions in many clinical conditions. In particular, variability of blood flow may occur as a consequence of hemodynamic instability related to changes in heart rate, cardiac arrhythmia, valvular or congenital heart disease, and application of mechanical ventilation. Additional limitations of the thermodilution method are its invasiveness and the impossibility of monitoring CO beat-to-beat in critical conditions and during the course of acute pharmacological interventions.

The direct oxygen Fick approach is the standard reference technique for CO measurement. See, for example, Fagard, R. and Conway, 3 (1990), "Measurement of cardiac output: Fick principle using catheterization," Eur. Heart J. 11, Suppl. I, pp. 1–5. According to the Fick principle, CO can be determined by the ratio of oxygen uptake to the difference in oxygen content between arterial and mixed venous blood. The validity of the principle depends upon the assumption that pulmonary blood flow is approximately identical to systemic blood flow and that the lungs themselves do not extract oxygen. Although this method appears to be the most accurate among those currently available, its use is limited by a series of practical problems. These problems include the need for right heart catheterization to obtain truly mixed venous blood, the assumption of the availability of appropriate analytical techniques for measuring oxygen uptake and content, and the attainment of a steady state in which apparent oxygen consumption matches tissue oxygen utilization. The fulfillment of these conditions makes the method unsuitable for repeated measurements and, consequently, not apt to follow rapid changes in flow over time.

The pulse contour method (PCM), which has been developed from an original idea by J. A. Herd et al. dating back to 1864 and from a theory commonly referred to as the "Windkessel" (German for "air chamber") theory of Franck (Franck O., 1930), derives CO from the arterial pressure pulse wave. The PCM method is based on the existence of a relationship between the volume of blood expelled by the left ventricle (LSV) or the volume of blood expelled by the right ventricle (RSV) and the area under the pressure curve P(t). Unlike the thermodilution and Fick methods, which measure mean CO over a limited time span, the PCM operates on a beat-to-beat basis. The primary assumption of PCM is that the pressure rise during systole is related, in a complex way, to the systolic filling of the aorta and proximal large arteries. Various approaches have therefore been devised to approximate, by means of different models of the arterial system, the relationship between aortic pressure and flow.

One of the most famous models used in PCM was developed by Wesseling and his co-workers and is described in, among many other references:

Wesseling, K. H., De Wit, B., Weber, J. A. P. and Smith, N. T. (1983), "A simple device for the continuous measurement of cardiac output. Its model basis and experimental verification," Adv. Cardiol. Phys. 5, Suppl II, pp.16–52;

Wesseling, K. H., Jansen, J. R. C., Settels, J. J. and Schreuder, J. J. (1993), "Computation of aortic flow from pressure in humans using a nonlinear, three-element model," J. Appl. Physiol. 74, pp. 2566–2573;

Jansen, J. R. C., Wesseling, K. H., Settels, J. J. and Schreuder, J. J. (1990), "Continuous cardiac output monitoring by pulse contour during cardiac surgery," Eur. Heart J. 11, Suppl 1, pp. 26–32;

Sprangers, R. L., Wesseling, K. H., Imholz, A. L., Imholz, B. P. and Wieling, W. (1991), "Initial blood pressure fall on stand up and exercise explained by changes in total peripheral resistance," J. Appl. Physiol. 70, pp. 523–530;

Jellema, W. T., Imholz, B. P. M., van Goudoever, J., Wesseling, K. H. and van Lieshout, J. J. (1996), "Finger arterial versus intrabrachial pressure and continuous cardiac output during head-up tilt testing in healthy subjects," Clin. Sci. 91, pp.193–200;

Stock, W. J., Baisch, F., Hillebrecht, A., Schulz, H. and Karemaker, J. M. (1993), "Noninvasive cardiac output measurement by arterial pulse analysis compared to inert gas rebreathing," J. Appl. Physiol. 74, pp. 2687–2693;

Harms, M. P. M., Wesseling, K. H., Pott, F., et al. (1999), "Continuous stroke volume monitoring by modelling flow from non-invasive measurement of arterial pressure in humans under orthostatic stress," Clin. Sci. 97, pp. 291–301;

Houtman, S., Oeseburg, B. and Hopman, M. T. E. (1999), "Non-invasive cardiac output assessment during moderate exercise: pulse contour compared with C02 rebreathing," Clin. Physiol. 19, pp. 230–237;

Jellema, W. T., Wesseling, K. H., Groeneveld, A. B. J, Stoutenbeek, C. P., Thjis, L. G. and van Lieshout, J. J. (1999), "Continuous cardiac output in septic shock by simulating a model of the aortic input impedance. A comparison with bolus injection thermodilution," Anesthesiology 90, pp.1317–1328;

Langewouters, G. J., Wesseling, K. H. and Goedhard, W. J. A. (1984), "The static elastic properties of 43 human thoracic and 20 abdominal aortas in vitro and the parameters of a new model," J. Biomech. 17, pp. 425–435; and Stock, W. J., Stringer, R. C. 0. and Karemaker, J. M. (1999), "Noninvasive cardiac output measurement in orthostasis: pulse contour analysis compared with acetylene rebreathing," J. Appl. Physiol. 87, pp. 2266–2273.

The Wesseling method is based on a model of the elastic properties of the aorta and has been found to be satisfactory under certain hemodynamic circumstances. According to the "Modelflow" method developed by Wesseling and coworkers, uncalibrated values of CO are obtained by relating the area under the pulsatile systolic portion of the pressure wave to parameters derived from a nonlinear three-element model of the arterial system. In PCM, in order to establish a relationship between pressure and flow, the mechanical properties of the arteries, as function of arterial pressure, are approximated either by several empirical formulae or by using a model based on age- and sex-predicted values not directly pertaining to the subject under study.

The three elements of the model used in Modelflow are aortic characteristic impedance (i.e., the relationship between the rise of pressure in the aortic root in opposition to the flow of blood ejected from the left ventricle), arterial compliance (i.e., the relationship between changes in blood volume and changes in pressure in the aorta), and peripheral vascular resistance (i.e., the relationship between mean pressure and mean flow). The first two elements of the model—impedance and compliance—depend mostly on the elastic properties of the aorta. In Modelflow, these elements are predicted by an experimentally derived arctangent function that relates aortic pressure and cross-sectional area; however, this prediction has, as required input variables, the age and sex of the subject. The third element—vascular resistance—is derived from the model simulation and is calculated and updated for the next heartbeat by the ratio between mean pressure and the computed flow.

Compared to other methods, the major advantage of PCM is the ability to monitor CO beat-to-beat over prolonged periods without the need of an indwelling pulmonary artery catheter for recording temperature changes or for blood sampling. Indeed, measurements can be derived from the pressure recordings in a systemic peripheral artery or even from the pressure signal detected noninvasively at the finger. The results of the method rely on the aortic pressure-cross-sectional area relationship, which is approximated from unrelated in vitro measurements on segments of human thoracic aorta. To obtain absolute values of CO, it is then necessary to determine, at least once for each patient, a calibrating factor of the model parameters by comparison of the PCM result with an absolute CO estimate—without such calibration, PCM can provide only relative changes in CO. The need for comparison with a reference method greatly limits the usefulness of PCM since the calibrating technique is either invasive (e.g., thermodilution) or cumbersome (e.g., inert gas rebreathing) and it must be repeatedly applied when changes in the experimental procedure, which may alter the physical properties of the arteries, are induced.

The estimates of CO by Modelflow thus depend more on fixed predicted parameters than on actual measurements obtained from the subject under evaluation. In fact, the parameters to measure CO derived directly from the pressure wave are limited to pulsatile systolic area, mean blood pressure, and heart rate. Other parameters that characterize the elastic properties of the arteries and that can be derived from the shape of the pressure curve, such as the time of attainment of peak systolic pressure, the presence of sudden slope changes, and the length of the diastolic phase, are not taken into consideration for the computation of CO. As a consequence, different forms of the pressure signal and different end-diastolic pressure levels can result in pulsatile systolic areas with comparable integral value. It is likely, however, that pressure waves with markedly different contours and end-diastolic pressure levels may reflect definite differences of arterial vessels physical characteristics even though they have similar pulsatile systolic areas. As such, accurate computation of CO using Modelflow and related methods is highly dependent on the measurement of a calibrating factor derived by comparison with an independent standard reference method, rather than on the actual pressure wave morphology.

What is needed is therefore a method for measuring accurately an absolute value of CO, that is, which does not require calibration using some other absolute method, and that can do so continuously for prolonged periods. The method should preferably be able to accomplish this without the level of invasiveness of, for example, thermodilution methods, and it should not depend on such patient-specific parameters such as weight, height, body surface area, sex, age, the diameter of the aorta of the patient, etc. This invention provides such a method, and a related system for implementing it.

SUMMARY OF THE INVENTION

The invention provides a method for measuring cardiac output (CO) of a patient, as well as a system that implements the method. According to the invention, arterial blood pressure is sensed and is converted to a pressure signal. An estimate of stroke volume is then calculated as a function only of selected characteristics of the sensed pressure signal and of predetermined, patient unspecific constants. The invention then calculates an estimate of CO as a function of the estimated stroke volume and a current heart rate value.

In the preferred embodiment of the invention, the estimate of stroke volume is calculated by calculating an area (A) under the entire pressure signal, including both pulsatile and non-pulsatile portions of the pressure signal, over a cardiac cycle; estimating selected impedance values from the pressure signal; and calculating the estimate of stroke volume as a function of the ratio between the calculated area and the estimated selected impedance values.

As part of calculating the estimate of stroke volume, the invention preferably also calculates a mean pressure value of the pressure signal and then corrects the estimated stroke volume as a predetermined function of the mean pressure value and of a reference pressure.

The preferred embodiment of the invention detects the times and corresponding pressure values of a systolic peak and of a dicrotic notch in the pressure signal. A second derivative of the pressure signal is then evaluated between the systolic peak and the dicrotic notch. The time and corresponding pressure value of at least one intermediate point in the pressure signal are then detected between the systolic peak and the dicrotic notch at which the second derivative has an extreme value and at least one of the selected impedance values is then estimated as a predetermined function of the time and corresponding pressure value of the intermediate point.

A systolic peak pressure $P_{sys}$, a diastolic pressure $P_{dia}$, and a dicrotic pressure $P_{dic}$ are preferably detected and the estimated stoke volume is then preferably scaled by a factor proportional to the ratio between the difference between $P_{dia}$ and $P_{dic}$ and the difference between $P_{sys}$ and $P_{dia}$.

In addition to detecting a dicrotic notch in the pressure signal, in some embodiments of the invention, a post-dicrotic first derivative of a post-dicrotic portion of the pressure signal is also evaluated at times after the dicrotic notch. In these cases, the time and corresponding pressure value of at least one local maximum pressure are detected in the post-dicrotic portion of the pressure signal and at least one of the selected impedance values is estimated as a predetermined function of the time and corresponding pressure value of the local maximum pressure.

Using the preferred embodiment of the invention, the CO estimate may be calculated based on the pressure signal during a single cardiac cycle.

In the preferred embodiment of the invention, the pressure signal is uncalibrated, whereby the steps of calculating the estimate of the stroke volume and of calculating the estimate of CO are independent of external calibration.

The invention thus provides for direct calculation of cardiac flow (or, equivalently, cardiac output) and arterial impedance (Z) from a measured pressure signal. The pressure signal may be measured either invasively, for example, in the ascending aorta, or in the pulmonary, femoral, brachial, or radial artery, or non-invasively, for example from the arteriole of the finger using a cuff meter. A composite impedance value $Z_{tot}$ of the pressure signal is calculated directly on the basis of characteristics of various resonance points, preferably by means of an analysis of the first and second time derivatives of the pressure signal.

In determining stroke volume SV, from which the invention calculates cardiac output, the invention takes into account both pulsatile and non-pulsatile (continuous) components of the recorded pressure signal. Accordingly, in calculations of SV, the invention considers the area A under the entire pressure signal, that is, the pulsatile portion above the diastolic pressure as well as the continuous portion below the diastolic pressure. Moreover, with respect to the composite impedance $Z_{tot}$, in addition to the pulsatile portion between the time of diastoly and the dicrotic notch, the invention also takes into consideration the influence of the non-pulsatile, continuous portion of the pressure curve that occurs after the dicrotic notch.

The invention is therefore able to calculate the cardiac flow with no need to calibrate the recorded pressure signal, and no need to incorporate patient-specific, anthropometric data. Rather, the invention determines SV exclusively from an analysis of the characteristics of the pressure wave itself. These characteristics include not only the "principle" balancing points (systolic and dicrotic points) of pressure of ventricularly ejected blood, but also of additional points of balance.

DETAILED DESCRIPTION

Introduction

The invention provides a method for measuring cardiac output (CO) solely through analysis of the arterial pressure contour. One exemplary embodiment of the invention is directed to an invasive pressure measurement from the catheter-mounted pressure sensor located, for example, in the ascending aorta. In another embodiment the pressure sensor is positioned in the pulmonary artery. Further embodiment of the invention is completely non-invasive and senses pressure using an external pressure device, for example, a photo-plethysmographic blood pressure probe mounted on a patient's finger. Still another examplary embodiment of the invention is invasive, but minimally so, and uses a catheter-mounted pressure sensor that is inserted in a peripheral artery such as the femoral, brachial or radial artery. In all embodiments, the underlying method is the same. Before discussing specific embodiments, however, the general method according to the invention is described. Specific implementations of the general method are then described, as well as the main components of a system for implementing the method according to the invention. Finally, the results of tests of the invention are summarized.

General Cardiac Output Measurement Method

Figure 23:
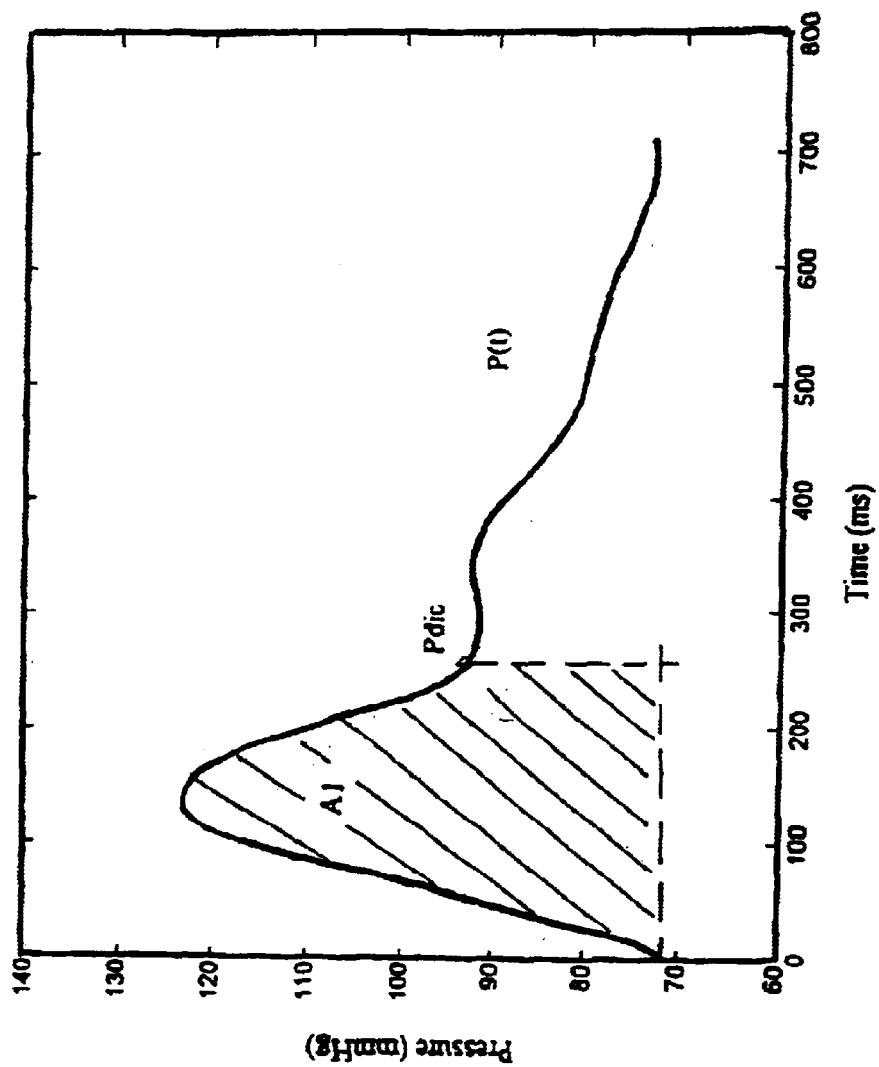
FIG. 23 illustrates a cardiac pressure signal diagram or profile as it would typically appear when sensed and analyzed using a prior art method.

FIG. 23 illustrates a typical pressure profile or pressure wave during one heart beat as it would be analyzed and as stroke volume and cardiac output would be determined under the prior art conventional pulse contour (PCM) method. In conventional PCM methodology, the conversion from pulse-stroke (mmHg×sec) to stroke volume (cm$^3$) is obtained from the area A1 under the pulsatile systolic portion of the pressure wave, weighed by a factor Z that represents the impedance, which in turn depends upon the dynamic resistances and upon the compliance of the arterial wall. Stroke volume (SV) can be derived as:

$$SV = A1/Z--;$$

Note that, as shown in FIG. 23, in all known PCM systems, the area under the pressure curve that is taken into consideration in determining SV is only the area shown with hatch lines and identified as area A1. A value of A1, derived from the pressure curve P(t) is therefore computed based only on the area under the pressure curve greater than the diastolic pressure, that is, under the pulsatile systolic area from the start of the upstroke, shown at slightly above 70 in FIG. 23 (pressure of aortic valve opening) to the dicrotic notch (pressure of aortic valve closure). As FIG. 23 illustrates, the area used in prior art methods is evaluated as:

$$A1 = \int_{t0}^{tdic} [P(t) - Pdia] dt$$

The drawback of prior art methods of evaluating area is thus that it fails to take into account the relative level of pressure at the valve opening, even though this pressure level is the expression of the balance between the force of ejection of the left ventricle (upstream) and the physical characteristics of the arterial system (downstream). As is known, SV is the result of both a pulsatile component and a continuous component; the prior art, however, typically fails to evaluate and consider both of these components.

Figure 1:
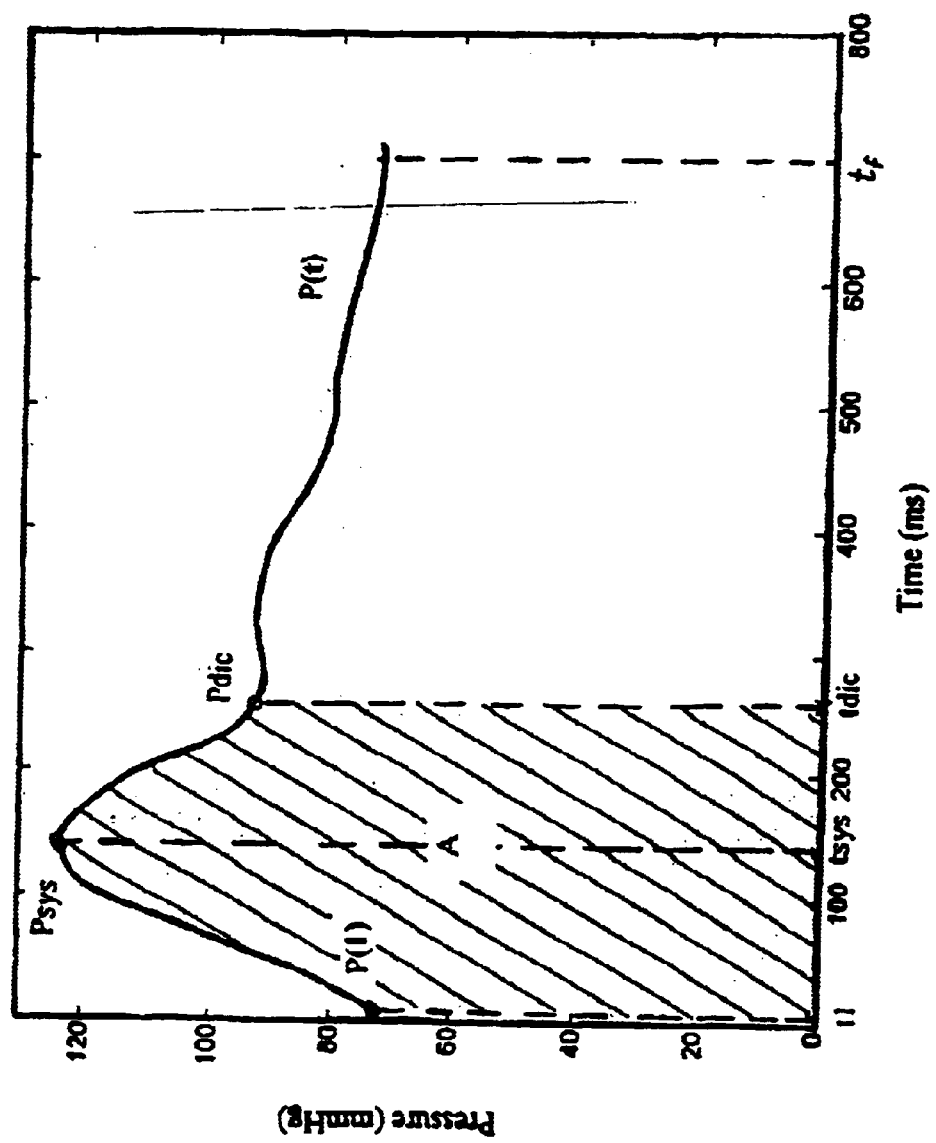
FIGS. 1–19 illustrates pressure signal profiles as they are sensed at various points in or on a patient's body and as they are used in the invention; in particular, these figures illustrate that the signals used in the invention include information about both first and second derivatives of the pressure.
Figure 2:
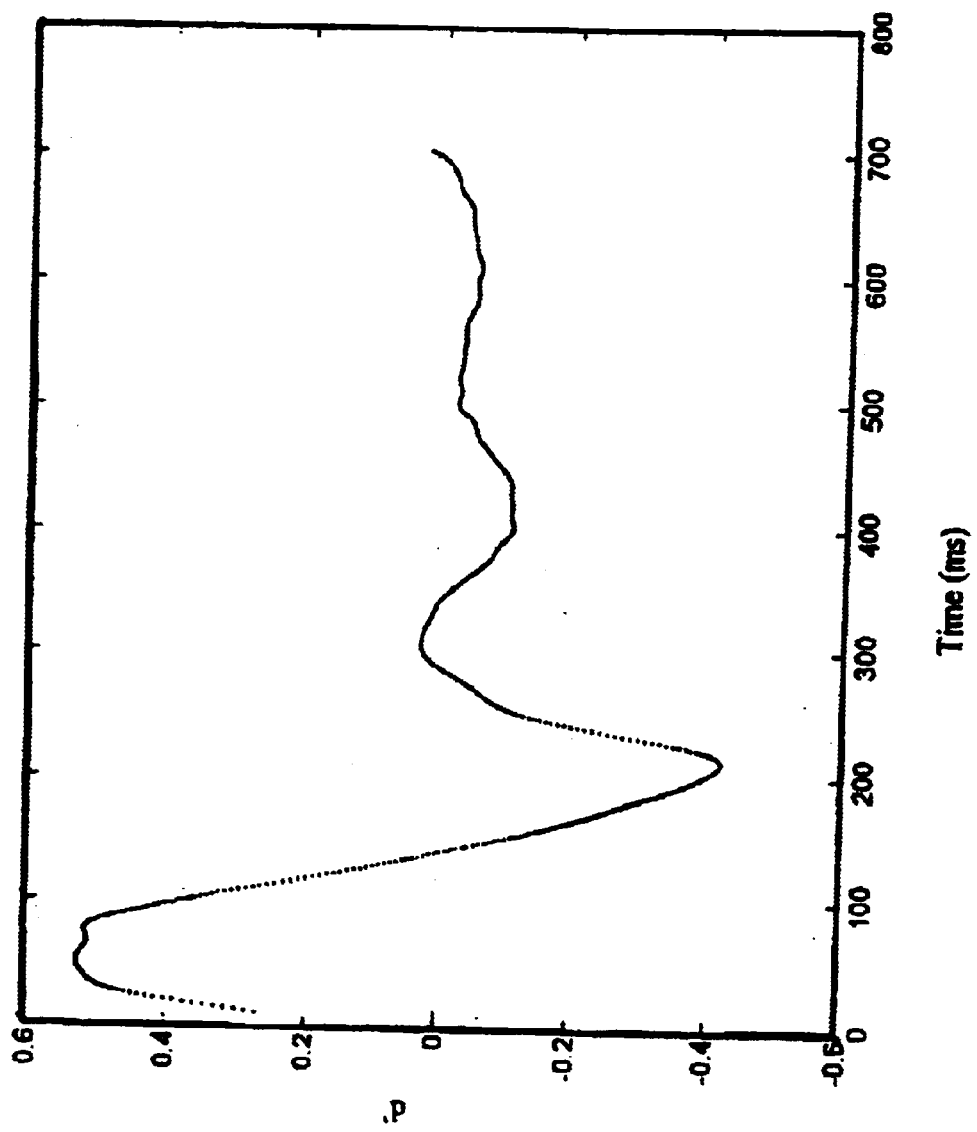
Figure 3:
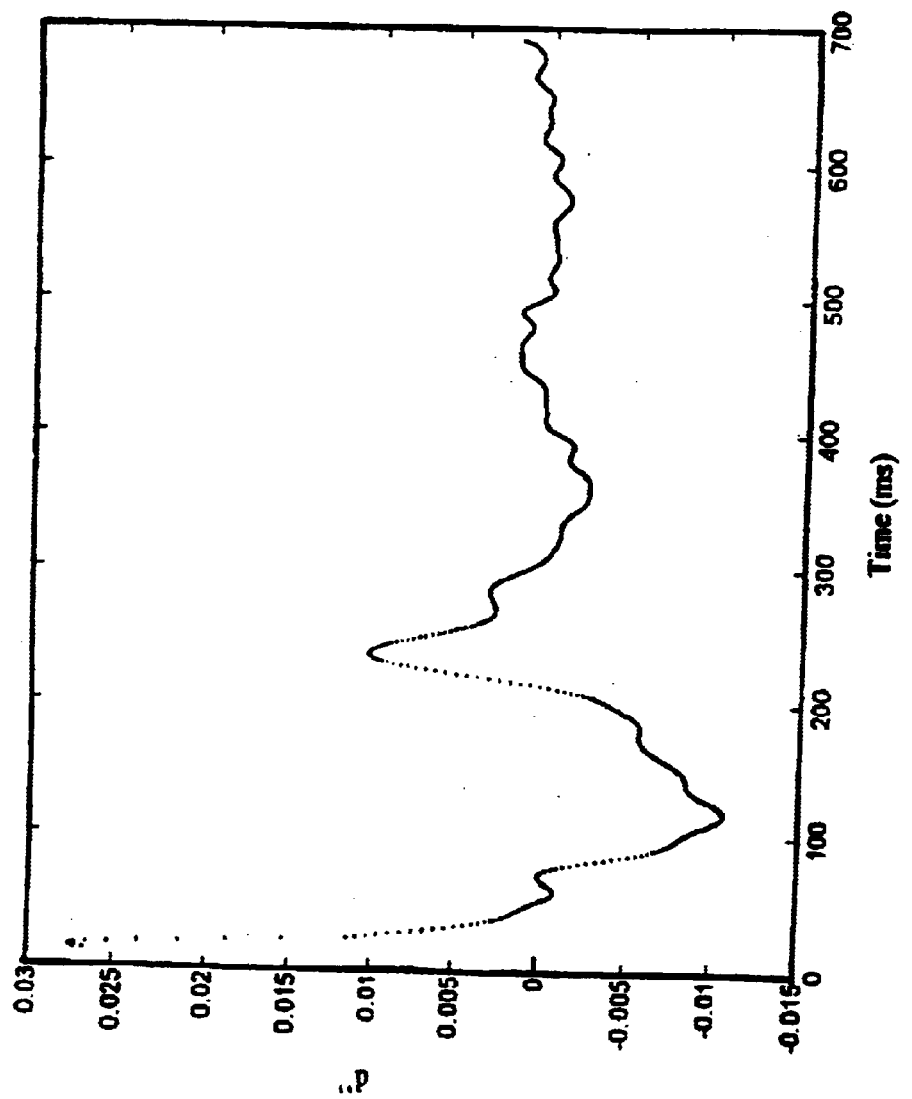

FIG. 1 illustrates a typical pressure profile P(t) of arterial blood during one heart beat, from an initial time t=t1=0 to a final time $t=t_f$. The initial time t1 is chosen to be the beginning of the systolic phase, that is, the point where the pressure begins to rise at the beginning of the cardiac cycle; this point may be determined using any known method. The pressure and time scales are expressed in mmHg and ms, respectively, for the sake of clarity. Although the pressure curves shown in the various figures are representative of those that appeared during the actual tests of the invention, as it is understood by those skilled in the art, they should be viewed qualitatively rather than quantitatively.

One difference between the invention and the prior art is immediately visible in FIG. 1, namely, the manner in which the invention evaluates area for use in calculations: as shown by the shaded portion of FIG. 1, the invention calculates the whole area A under the systolic portion of the pressure curve in order to determine a value of area:

$$A = \int_{t0}^{tdic} P(t)dt$$

The invention thus includes both pulsatile and non-pulsatile (continuous) contributions to reflect more accurately the effects of the physical forces that determine the relationship between the morphology of the arterial pressure profile and blood flow.

Each point of the pressure waveform P(t), registered from a systemic arterial vessel, is the result of a dynamic equilibrium among physical phenomena taking place upstream and downstream along the transmission line of the pressure wave from the left heart to the peripheral arteries. These physical phenomena can be summarized as: 1) the force of ejection of blood generated by the left ventricle; 2) the arterial impedance that counteracts the pulsatile inflow of blood; 3) the arterial compliance that permits the artery to elastically store a portion of the kinetic energy of the cardiac upstroke; and 4) the resistance of the peripheral vessels that generates backwards reflections of the pressure wave, depending on heart rate (HR) and relative tightening, bifurcations, and stiffness of downstream arterial vessels.

According to the present invention, the impedance Z is determined as follows:

$$Z=1/K*P/t$$

where P/t reflects the morphology of the pressure wave contour as variations of pressure P with time (t) along each cardiac cycle and K is a dimensional factor.

In peripheral arteries, the pressure wave profile P(t) is characterized by a steeper upslope reaching a higher systolic peak $P_{sys}$ with respect to the central arteries, whereas the diastolic pressure $P_{dia}$ and the mean pressure are lower. Assuming that volume changes occur mainly because of radial expansion of the vessel wall in response to a change in pressure, Z establishes the relationship between pressure changes and volume changes with time in the vessel in which the arterial pressure wave is recorded.

The factor K is inversely related to the instantaneous acceleration of the vessel cross-sectional area, whose numerical value is approximated by the ratio between expected (under physiologic conditions) and measured mean blood pressure. In many cases, K may be assumed to be equal to unity without significant loss of accuracy. The value of K will differ from unity, however, in the presence of physical phenomena that may affect the pressure wave transmission. Examples of these phenomena include low stroke output from the left ventricle and backwards wave reflections from the peripheral vasculature. Since the perturbations of the pressure wave are typically reflected in the instantaneous acceleration of the arterial vessel cross-sectional area, the value of P/t is preferably corrected by assigning to K a value above or below unity by introducing a correction factor which is described in detail below in reference to Examples of some specific embodiments of the invention and in Equation C. This enables the invention to take into account in the computation of Z the deviation of the transmitted pressure wave from the physiologically assumed ideal.

In order to analytically compute P/t from the sensed pressure wave, the basic method according to the invention assumes that peak systolic pressure $P_{sys}$ and the pressure $P_{dic}$ at the dicrotic notch represent points of dynamic equilibrium among the various forces that arise as the blood flows in the arterial system.

According to the invention, and contrary to the conventional PCM, for each subject under study, P/t or, as used in the invention, $Z_{tot}$, is computed as a composite of different impedance terms directly from the analysis of the pressure wave itself, with no need to obtain or take into account data derived from unrelated in vitro measurements or calibrating factors derived by independent measurements of CO. In simplest form, $Z_{tot}$ is approximated by variation of pressure P over time t where all various portions of the pressure curve along each cardiac cycle, including the portion after the dicrotic notch, are taken into account.

In particular, the invention evaluates the following relationship:

$$P/t=Z_{tot}=(P_{sys}-P_{dia})/t_{sys}+P_{dic}/(t_f-t_{dic}) \qquad \text{(Equation A)}$$

Note that, with respect to impedance, the first term $(P_{sys}-P_{dia})/t_{sys}$ corresponds mainly to the pulsatile component of the pressure curve (Za1), whereas the second term $P_{dic}/(t_f-t_{dic})$ corresponds mainly to the non-pulsatile, continuous component (Za2).

Using the notation in FIG. 1, where $P_{dia}$ is shown as P(1)=P(t1), $(P_{sys}-P_{dia})/t_{sys}$ is the pressure difference between peak systolic pressure $P_{sys}$ and the diastolic pressure $P_{dia}$ at aortic valve opening divided by the elapsed time $t_{sys}$ during which the pressure change occurred. This term of the equation is mainly related to the impulse generated by the cardiac upstroke in the vessel where the pressure is recorded. On the other hand, the dicrotic notch on the pressure contour (at $t=t_{dic}$), corresponding to the aortic valve closure, is mainly the result of forces that depend strictly on the physical characteristics of the arterial system such as impedance, compliance, and peripheral resistance. These forces correspond, after the cardiac stroke output, to the closure of the aortic valve and the constant runoff of blood towards the periphery during the diastolic period. In the term $P_{dic}/(t_f-t_{dic})$, $P_{dic}$ is the pressure at the dicrotic notch, and $(t_f-t_{dic})$ is the duration of the diastole as determined by the difference between the whole length of the cardiac cycle $(t_f)$ and the time of valve closure $(t_{dic})$.

Note that although P(t) is illustrated as a continuous curve in FIG. 1 (and FIG. 21 as well), in actual implementations P(t) may be represented digitally as a set of sample values obtained using conventional techniques for sampling and analog-to-digital conversion. $P_{sys}$ and $P_{dic}$ may then be identified in the pressure curve P(t) in any known manner. Note, for example, that $P_{sys}$ typically corresponds to the maximum pressure value, which can be determined, for example, by sample-to-sample comparison after the beginning of the cardiac upstroke—the point after which the values begin to decrease can be assumed to be the maximum value of P(t), which can then be taken as $P_{sys}$. In the preferred embodiment of the invention, however, $P_{sys}$ is determined by first evaluating the first time derivative P'(t) of the pressure curve P(t) during the systolic phase. $P_{sys}$ is then the point where the first derivative $d'=P'(t)=0$ (at $t=t_{sys}$). The second time derivative $d''=P''(t)$ is also evaluated. The point at which this second derivative P''(t) attains its maximum, after the $t_{sys}$, is then taken to be $P_{dic}$. The first and second time derivatives of P(t) can then be determined using any known numerical algorithms, such as any of the well-known difference methods.

The value P/t can thus be considered to reflect the morphology of the pressure wave as variation of pressure with time during the whole cardiac cycle. The relationship expressed in Equation A will typically be valid when the pressure contour between $P_{sys}$ and $P_{dic}$ is generally monotonically decreasing, as is illustrated in FIG. 1.

Figure 4:
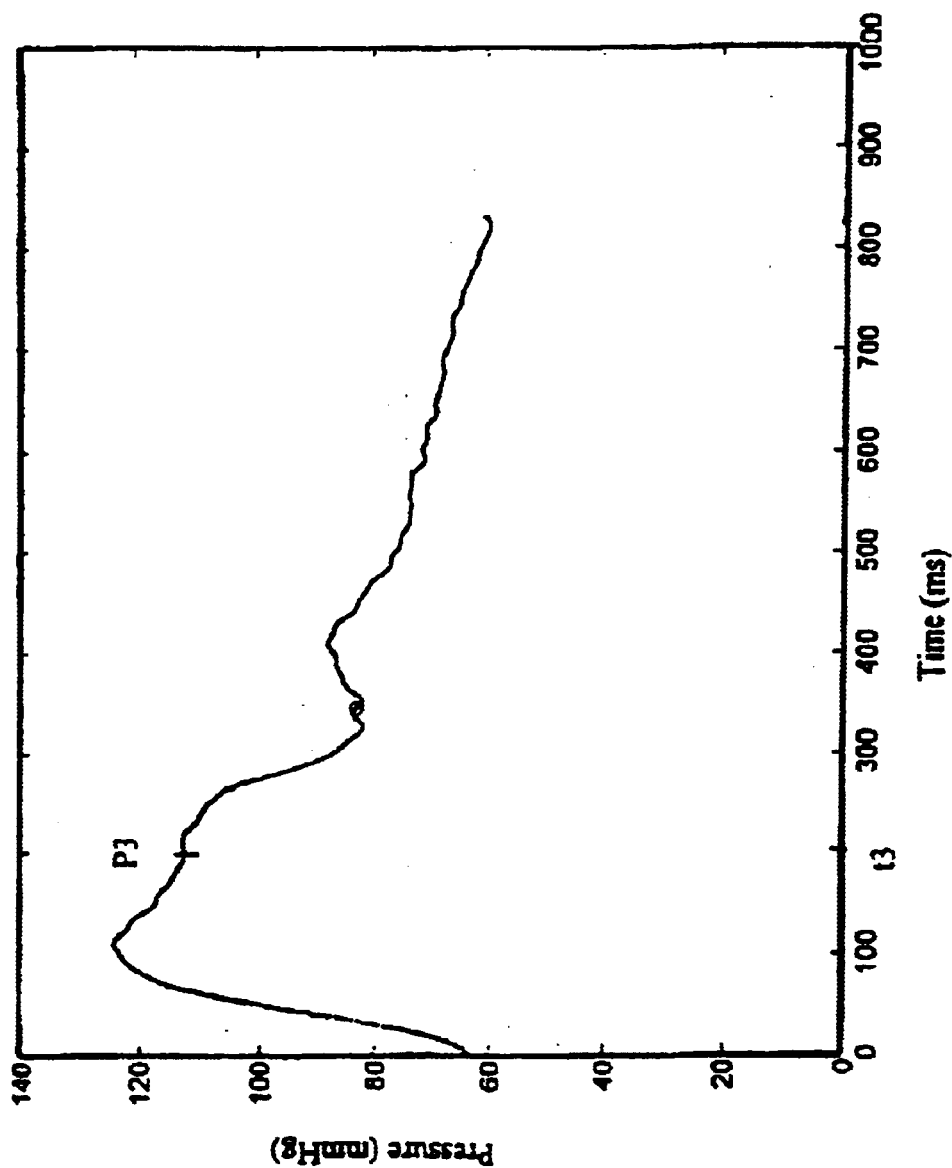
Figure 11:
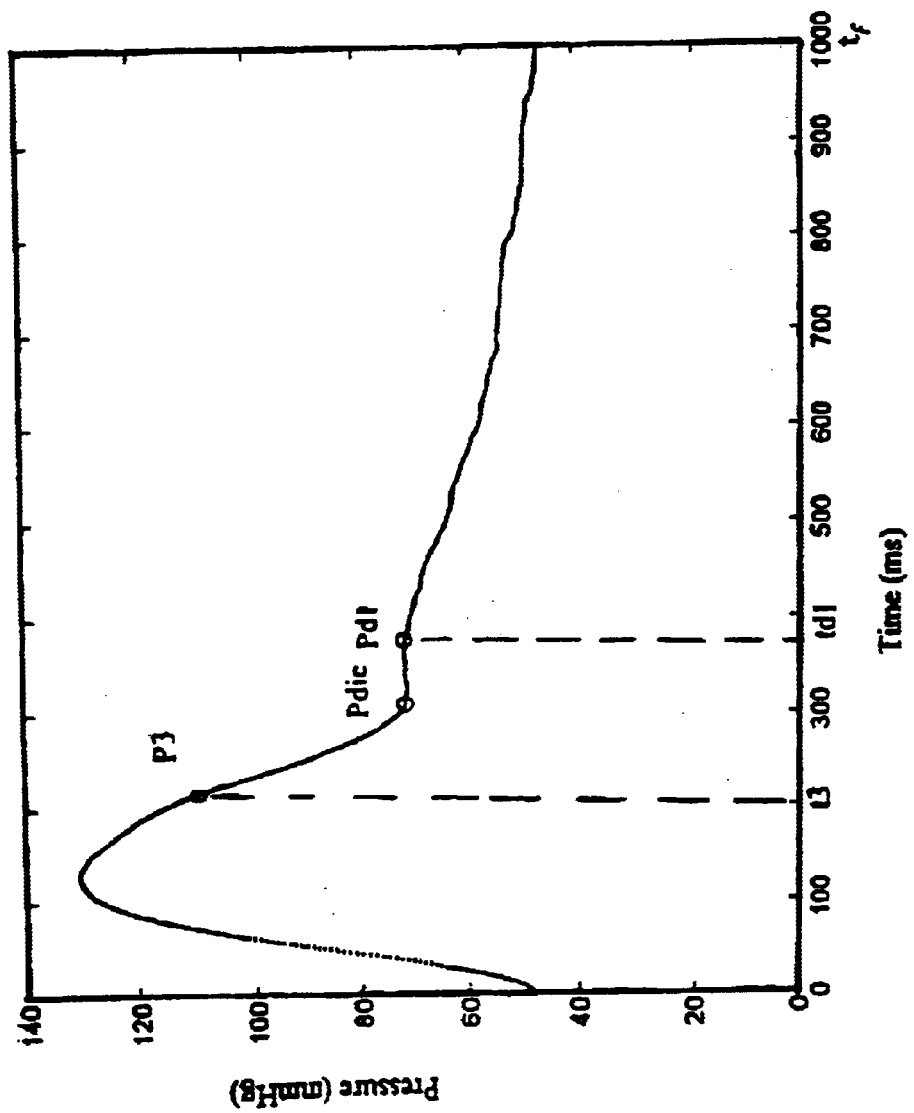
Figure 21:
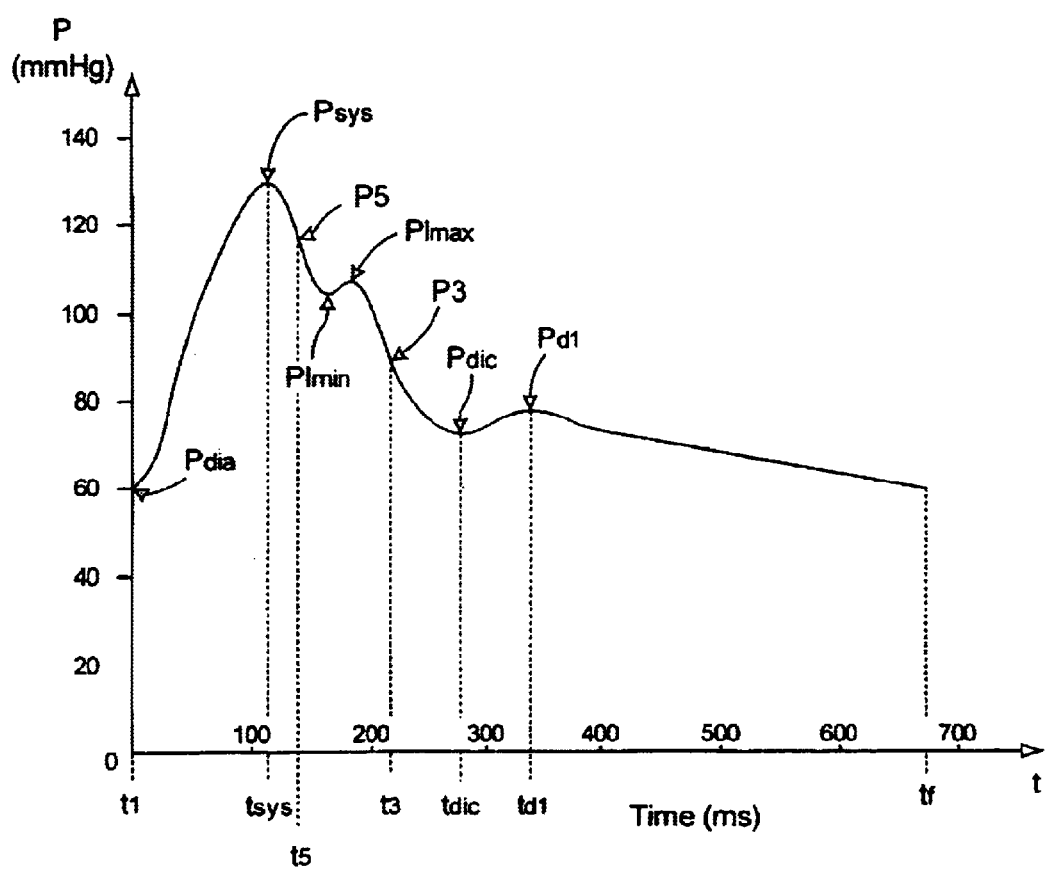
FIG. 21 is an illustrative example of a complex pressure curve, which shows different parameters used in various embodiments of the invention shown in FIGS. 1–19 and described in the Examples 1–4.

Backward reflections of the pressure wave from the periphery may give rise to sudden variations in downslope between $P_{sys}$ and $P_{dic}$. This phenomenon is illustrated in FIGS. 4, 11, or 21. The instability of the dynamic equilibrium among the physical forces determining the arterial pressure wave appears, from the analytical standpoint, as a relative maximum value of the first derivative of the pressure curve between $P_{sys}$ and $P_{dic}$. (see FIG. 5). The relative maximum of the first derivative identifies qualitatively the possible presence of sudden velocity changes of the pressure wave between $P_{sys}$ and $P_{dic}$ indicating the presence of instability phenomena generated by backward reflections from the periphery, while a relative minimum of the second derivative between $P_{sys}$ and $P_{dic}$ defines quantitatively the instability contributions.

In these conditions, the appearance of the dicrotic notch on the pressure wave may be delayed, or, under some circumstances, even be caused to occur earlier. To account for changes in the morphology of the pressure curve caused by such instability phenomena, a further term is therefore preferably introduced into Equation A as follows:

$$P/t=Z_{tot}=(P_{sys}-P_{dia})/t_{sys}+P_{dic}/(t_f-t_{dic})\pm P3/(t_f-t3) \quad \text{(Equation B)}$$

where P3 is the pressure value on the pressure contour occurring at the time t3 of the relative minimum value of the second derivative of the pressure curve between $P_{sys}$ and $P_{dic}$ and where the third term will be subtracted when the appearance of the dicrotic notch is delayed and added when the appearance of the dicrotic notch occurs earlier. The instability phenomena occur more often in the case with high arterial rigidity and in peripheral arteries.

The equation B above used to describe P/t has three terms. The first term is mainly linked to the pulsatile phase of the cardiac cycle, the second term is mainly due to the non-pulsatile phase of the cardiac cycle. This second term may be taken as the first and most relevant term of an oscillating harmonic series. In absence of instability phenomena the above term may be considered to approximate the whole series. On the contrary, in the presence of instability phenomena, to better define the contribution of the oscillating series to the computation of P/t it is necessary to introduce a third term. Theoretically, a higher number of successive terms could be introduced. Since the contribute of the harmonic oscillating series to the derivation of P/t must be a real number of positive value (not tending to infinity), the successive terms of the series must have alternating positive and negative sign.

FIG. 21 illustrates an even more complicated pressure waveform that illustrates in one figure a variety of various actual embodiments that separately shown in FIGS. 1–19. FIG. 21 serves to illustrate the various values used in the calculations of various Examples 1–4 described below according to the invention. For example, a local minimum $P_{lmin}$ (at a time $t=t_{lmin}$) and a local maximum $P_{lmax}$ (at a time $t=t_{lmax}$) may occur between $P_{sys}$ and $P_{dic}$, as well as an additional point P5 (at a time $t=t5$) where the second derivative is at a maximum. The minimum and the maximum (that is, the extreme values) of the second derivative are indicators of equilibrium situations (minimum is "stable" and maximum is "unstable" equilibrium respectively). If present, these local characteristics can be detected and distinguished from the dicrotic notch point ($P_{dic}$) using conventional numerical techniques, because $P_{dic}$ will typically be the global minimum point, other than the end points of the cycle (at t1 and $t_f$). Between the dicrotic notch and the end of the cycle, there will also be a local maximum $P_{d1}$ (at time $t_{d1}$), after which the pressure profile generally decreases until the beginning of the following cardiac cycle. Even $P_{d1}$ can be detected using conventional techniques given the sampled values of the detected pressure. Known numerical and programming techniques may therefore be used to determine which profile (for example, FIGS. 1, 4, 7, 8, 11, 14, 17 or 21) any given pressure curve P(t) most closely corresponds to.

Once P/t is calculated, using either Equation A or Equation B, or in a case of more complicated pressure waveform using further modified Equations A or B accounting for the additional balancing points as illustrated in the Examples below, a current value of composite impedance $Z_{tot}$ may be determined. Then given a value of K, adjusted if necessary by the correction factor, the final value of impedance Z may be determined. Thereafter, the invention can calculate a value of the stroke volume SV for each heart beat using the standard formula SV=A/Z. As is well known, cardiac output CO can then be estimated as the product of SV and the heart rate HR for the same beat, that is CO=SV*HR. Note that HR may be determined either in a known manner, using conventional equipment, or it may be calculated as a function of the inverse of the time duration of the cardiac cycle. For example, if time is measured in ms, then HR, measured in beats per minute, will be equal to 60000/T, where T is the cardiac period ($t_f-t_1$).

Examples of Specific Embodiments

Equations A and B above give the general form of the method for calculating $Z_{tot}$ according to the invention. In the preferred embodiment of the invention, however, in calculation of the stroke volume SV, $Z_{tot}$ is adjusted, as was mentioned above, and additional correction factors are included in order to improve the accuracy of the invention in different actual applications of the invention. These different applications will vary, for example, with respect to whether left or right ventricular stroke volume (LSV or RSV) is being estimated, whether pressure is being measured directly in an artery or non-invasively using a finger pressure cuff, the extent to which the mean pressure Pm deviates from a predetermined reference pressure, and whether the pressure curve P(t) and $Z_{tot}$ are affected by various instability factors such as reflection. Different cases of various exemplary applications of the present invention are discussed below.

The general form of the formula used in the preferred embodiment of the invention is:
(Equation C):

$$SV = \frac{K}{C} * \left[\frac{A}{Z_{tot}} + \frac{A}{Z_{tot}} * \frac{Pm - K1}{K1}\right]$$

$$= \frac{K}{C} * \frac{A}{Z_{tot}} * \left(1 + \frac{Pm - K1}{K1}\right)$$

$$= \frac{K}{C} * \frac{A}{Z_{tot}} * \frac{Pm}{K1} = \frac{A}{Z_{tot} * \frac{K1}{Pm} * \frac{C}{K}}$$

where:
SV is either LSV or RSV;
is a scaling factor which will depend on the sampling frequency (for a 1000 Hz sampling frequency used in tests, for example, C=10⁶);
K=($\lambda$m*sqrt(2p/p)*$V_m$), which is expressed in the units [l³t²]; In most applications of the invention, K=1;
$\lambda_m$ is the mean wavelength, approximately equal to 10 m;
$\rho$ is the density of blood; and
$V_m$ is the mean velocity, approximately equal to 10 m/s.
As before, A is the entire area under the pressure curve P(t) from t=tdia (time at the diastolic pressure in [ms]) to tdic (time at the dicrotic pressure in [ms]), including the area below the horizontal line at P(1)=$P_{dia}$. See the hatched area A in FIG. 1. The are A will have the units [mmHg*ms];
$Z_{tot}$ is as defined above and is determined as a composite, preferably, a linear combination of different impedance components (such as Za1, Za2, etc.) that will differ depending on the application; $Z_{tot}$ is expressed in [mmHg/ms] and is described further below for each case;
$P_m$ is a mean pressure value, which is preferably adjusted for different pressure intervals as described below;
K1 is a reference pressure, used to calculate a correction factor below. K1 represents the normal physiologic (expected) mean arterial pressure in a corresponding location of the body. It does not depend on anthropometric data. In fact, K1 should be similar for everybody regardless of sex, age, height, and weight. For example, a value of mean arterial pressure of 120 mmHg indicates hypertension for both a young, tall, fat man and an old, small, thin woman. The values of expected pressures used as K1 for different embodiments of the present invention correspond to the generally accepted for the normal mean pressure in a healthy individuals. Specifically, in aorta and large arteries it is 100 mmHg and in small distributing arteries it is 90 mmHg; however, for the special case of the pulmonary artery, K1 is approximately equal to 19 because compliance in the pulmonary artery is particularly high. These values are reported in various authoritative sources, including for example, common textbooks of physiology.
The term (1+($P_m$-K1)/K1) is a correction factor based on the extent to which the mean pressure value $P_m$ deviates from the reference pressure K1.
To summarize, the invention therefore determines SV as a function of both a) the ratio between A and a linear combination of selected impedance values; and b) the ratio between a value of mean pressure ($P_m$) and a reference pressure K1. Once SV is calculated, the cardiac output CO, measured in liters per minute, can also be calculated in the conventional manner, since CO=SV*HR. In the examples of the invention described below, HR=60000/T, where T is the cardiac period ($t_f$-$t_1$), expressed in ms.
Different examples of the implementation of the method according to the invention will now be given, with the various parameters and values labeled as in FIGS. 1 and 21. As will be understood by those skilled in the art, the specific embodiments below are presented as examples only and they do not limit in any way the scope of the present invention.

EXAMPLE 1

Calculation of LSV when Pressure is Taken in the Ascending Aorta (FIGS. 1–6)

EXAMPLE 1A

In this example, pressure P(t) is measured in the ascending aorta and this pressure is used to estimate left ventricular stroke volume LSV. The pressure profile corresponds to the one illustrated in FIGS. 1–3. In this case, the relationship for determining LSV is as follows:

$$LSV = \frac{K}{1000}\left[\frac{A}{(Za1 + Za2)*1000} + \frac{A}{(Za1 + Za2)*1000} * \frac{(Pm - K1)}{K1}\right] \quad \text{(Equation 1)}$$

Normal algebraic transformation can be used to reduce this to the form of Equation C, with the following substitutions:

K1=100 mmHg (normal physiological pressure in the descending aorta)
$P_m$=($P_{sys}$+2*$P_{dia}$)/3
$Z_{tot}$=Za1+Za2
where:
Za1=($P_{sys}$-$P_{dia}$)/$t_{sys}$ [mmHg/ms]
Za2=$P_{dic}$/($t_f$-$t_{dic}$) [mmHg/ms]
The mean pressure value $P_m$ is preferably further adjusted according to the explanation provided in Note 1 below.

EXAMPLE 1B

Figure 5:
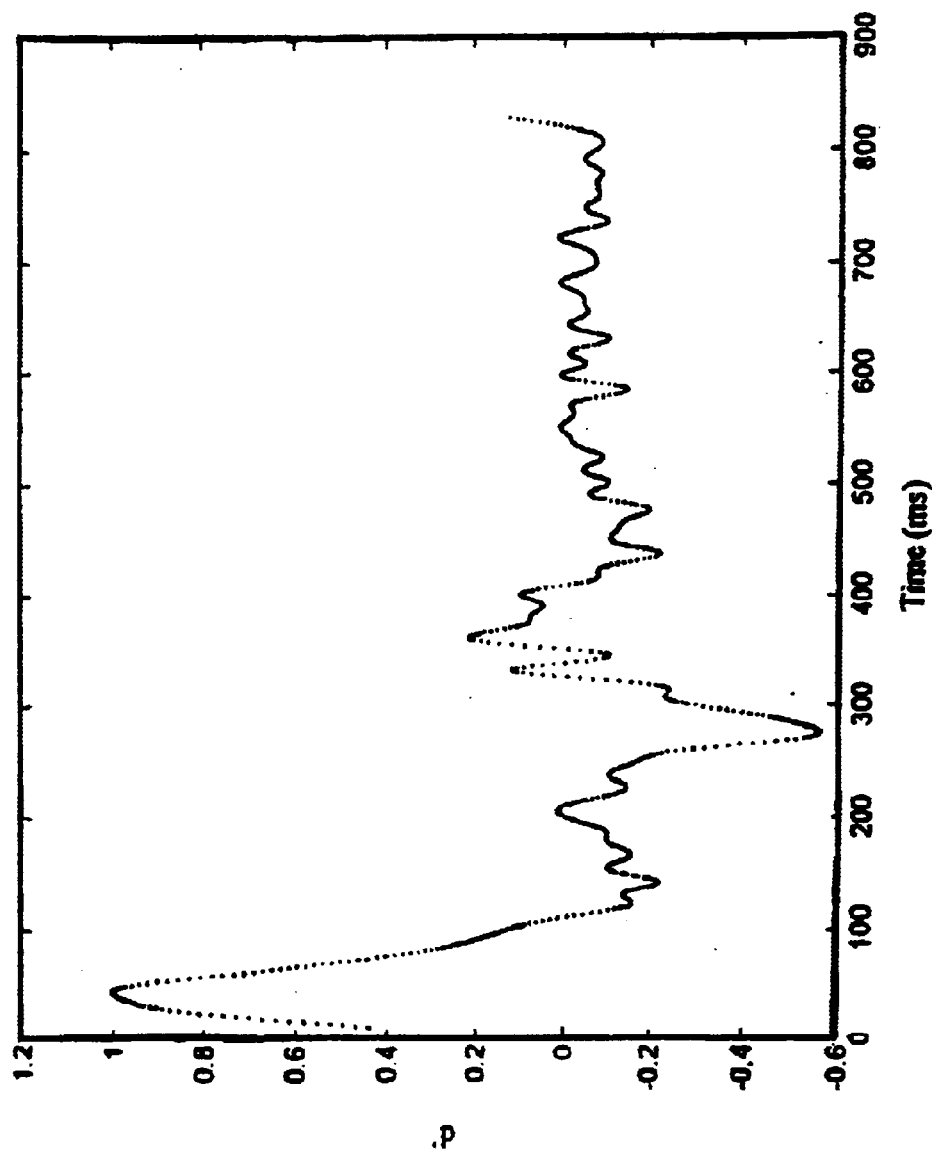
Figure 6:
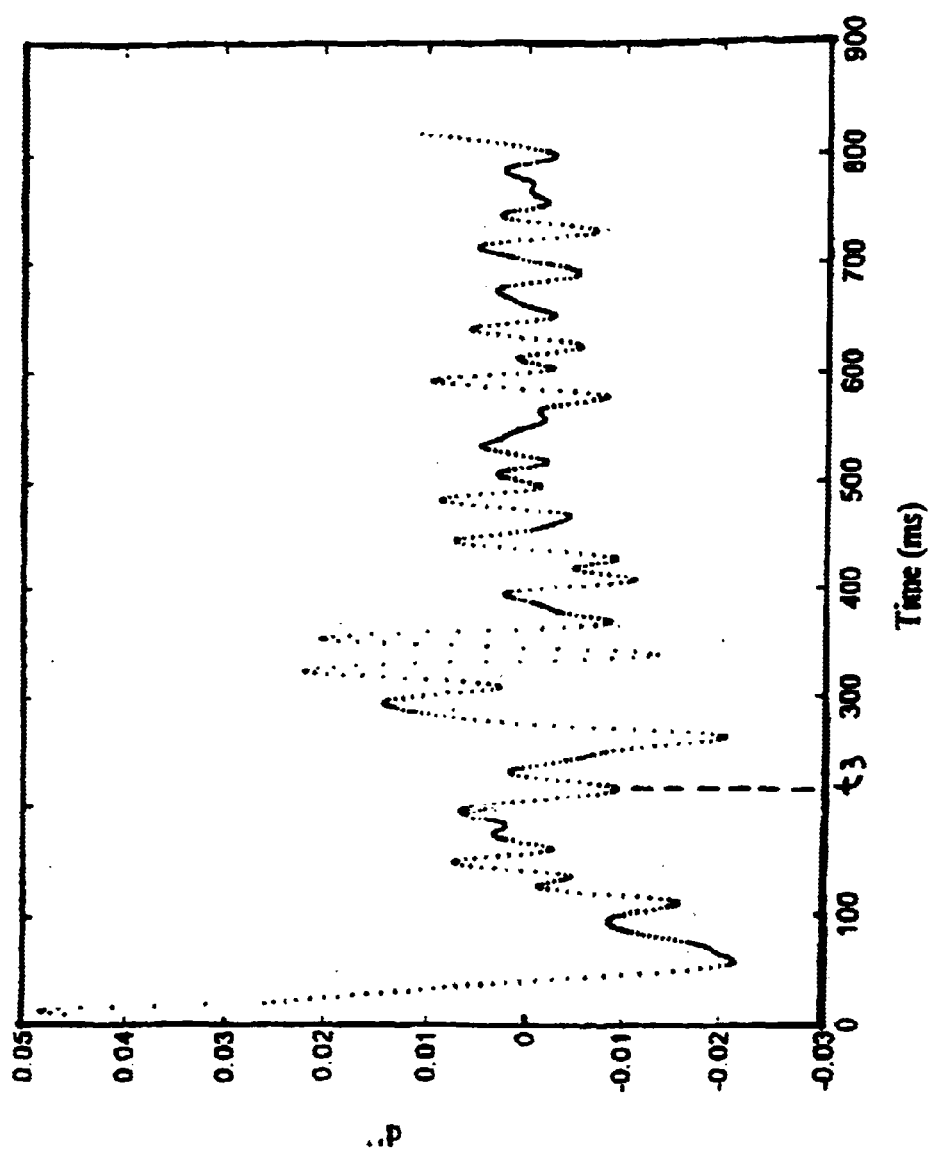

In the cases where the pressure curves in the ascending aorta were of the type shown in FIG. 4, and the corresponding first and second derivatives, d' and d", were as those shown in FIGS. 5 and 6, with a resonance point at time t3, the relationship and equation of Example 1A is then modified to become:

$$LSV = \frac{K}{1000}\left[\frac{A}{(Za1 + Za2 - Za3)*1000} + \frac{A}{(Za1 + Za2 - Za3)*1000} * \frac{(Pm - K1)}{K1}\right] \quad \text{(Equation 2)}$$

where:
Za3=P3/(tf-t3) mmHg/ms;
t3 is the time in [ms] when the minimum value of the second derivative d" between the time $t_{sys}$ and the time $t_{dic}$ (the resonance point) occurred; and
P3 is the corresponding pressure expressed in [mmHg] at time t3 (see FIG. 4).
In this example, as in Example 1A, pressure P(t) is thus measured in the ascending aorta and is used to estimate left ventricular stroke volume LSV. This formula may also be reduced to the form of Equation C.

$P_m$ is then calculated as in Example 1a. An extra component is introduced into the formula for $Z_{tot}$, however, as follows:

$$Z_{tot}=Za1+Za2-Za3$$

where Za1 and Za2 are as in Example 1A. Cardiac output may then be calculated in the usual manner, The ultimate calculation of the CO is based on the same base formula CO=SV*HR.

Note 1

In both Example 1a and Example 1b, the mean pressure value $P_m$ preferably further adjusted depending on to what extent $P_m$ deviates from the reference pressure K1, which, in the case of the ascending aorta is 100 mmHg. In the preferred embodiment of the invention, the amount of adjustment is "graduated," depending on the amount of deviation, which is classified by intervals, which were determined using normal experimental techniques. Of course, continuous adjustment functions may be applied, although this will typically not increase accuracy significantly.

The mean pressure $P_m$ for the pressure measured in the ascending aorta must be considered as such and the actual number should be used for the interval 90–110 mmHg; for the mean pressure between 110 and 120 mmHg, and between 90 and 80 mmHg, it must be considered at 50% (for example, for a measured Pm=118 mmHg, an adjusted value of 114 mmHg is used); for mean pressure values between 120 and 130 mmHg and between 80 and 70 mmHg it must be considered at 25%; and for mean pressure values greater than or equal to 130 mmHg and less than or equal to 70 mmHg it must be considered 13%.

According to the above, $P_m$ is thus adjusted to a new value $P_m^*$ as follows before being used in the expressions for LSV above:

For $$90<P_m<=110 \rightarrow P_m^*=P_m$$

$$110<P_m<=120 \rightarrow P_m^*=110+0.5^*(P_m-110)$$

$$120<P_m<=130 \rightarrow P_m^*=115+0.25^*(P_m-120)$$

$$P_m>130 \rightarrow P_m^*=117.5+0.13^*(P_m-130)$$

$$80<P_m<=90 \rightarrow P_m^*=90-0.5^*(90-P_m)$$

$$70<P_m<=80 \rightarrow P_m^*=85-0.25^*(80-P_m)$$

$$P_m<=70 \rightarrow P_m^*=82.5-0.13^*(70-P_m)$$

EXAMPLE 2

Figure 7:
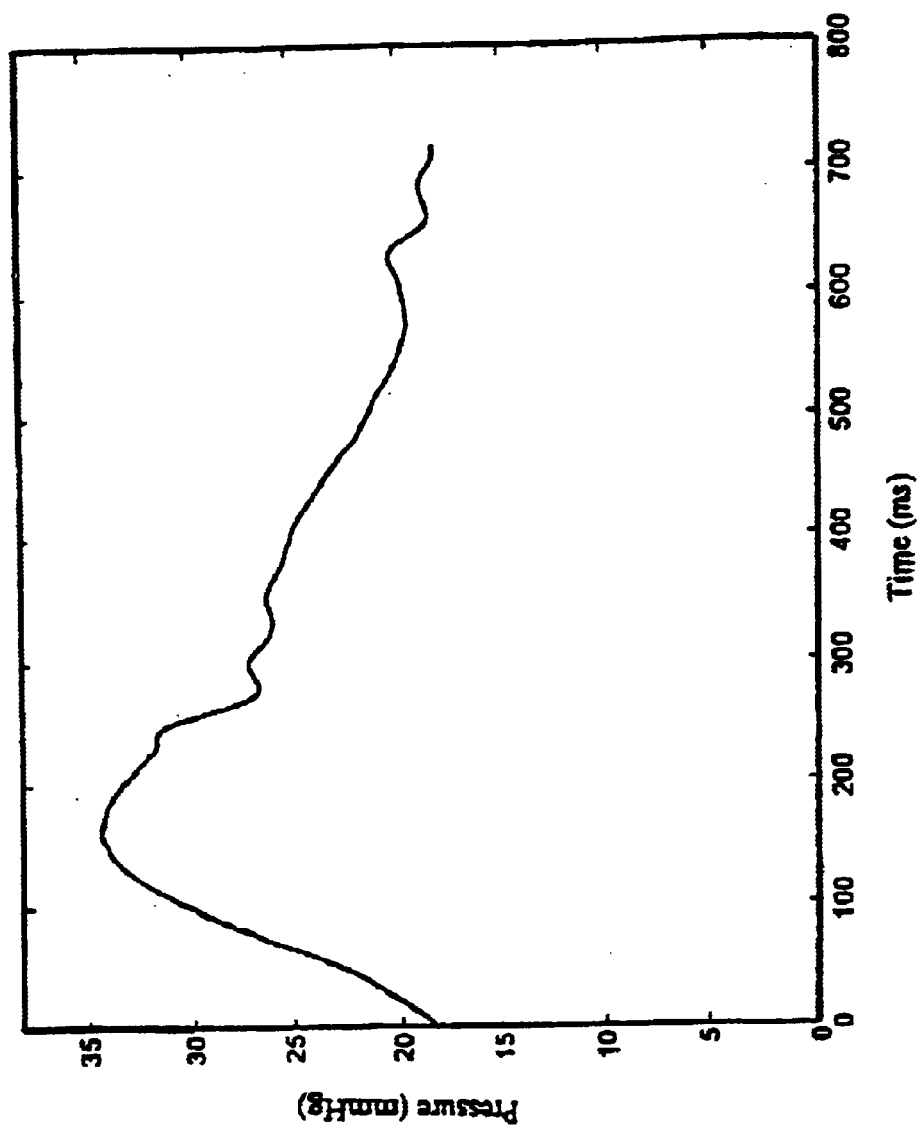
Figure 8:
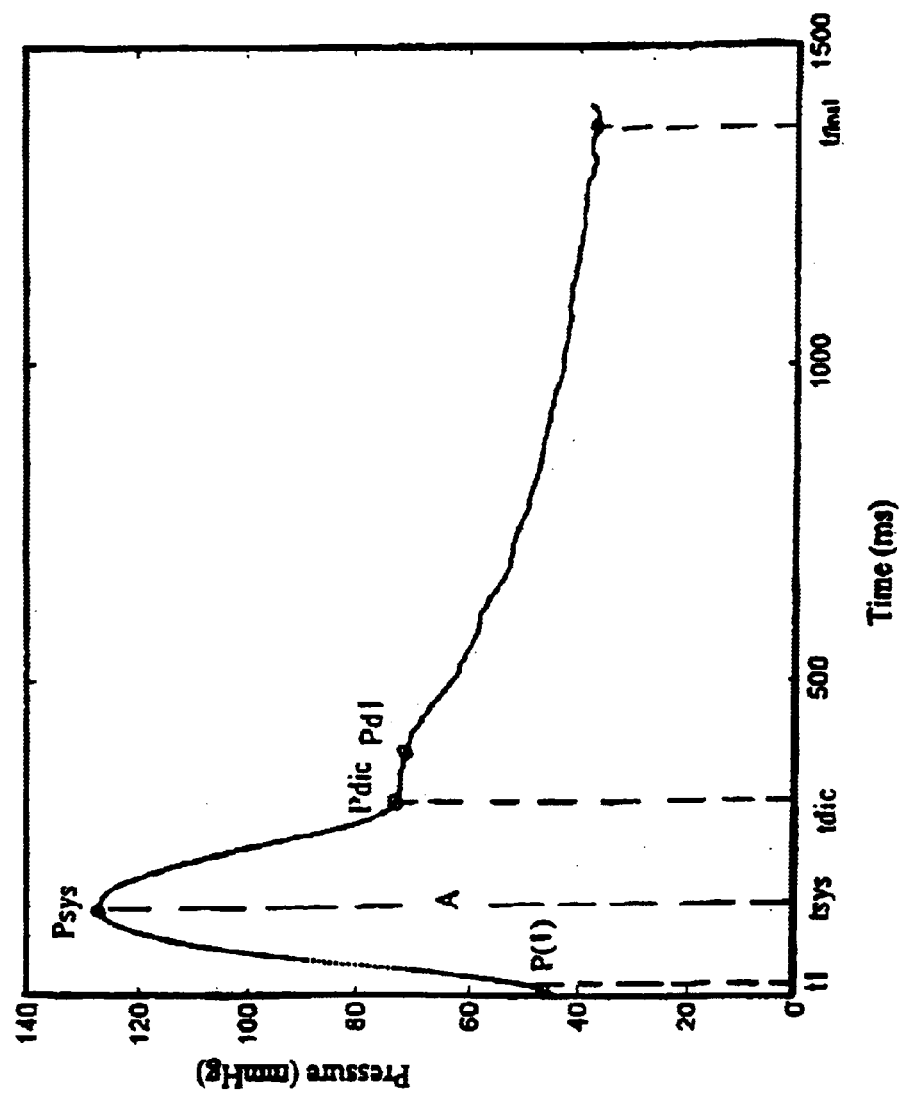
Figure 9:
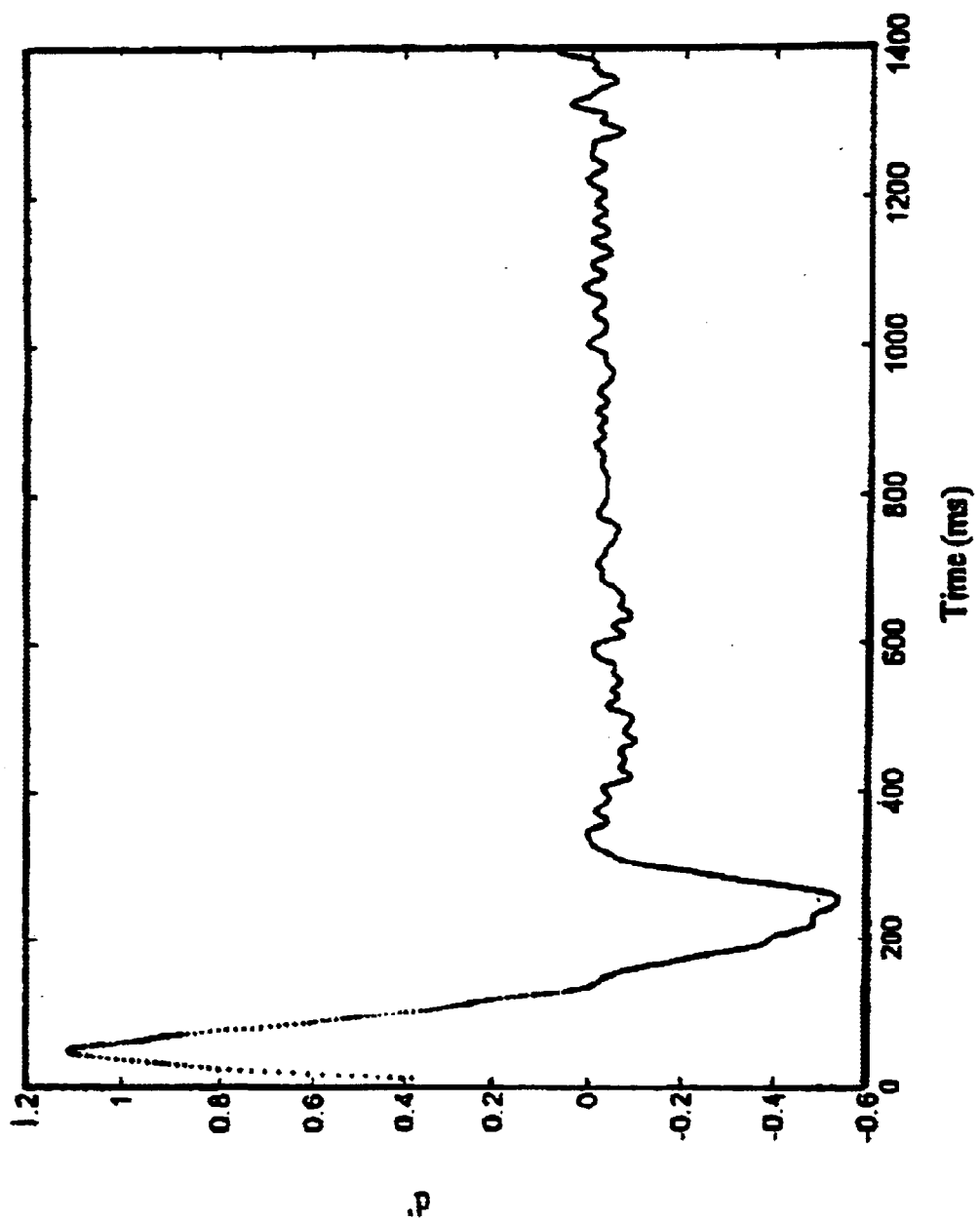
Figure 10:
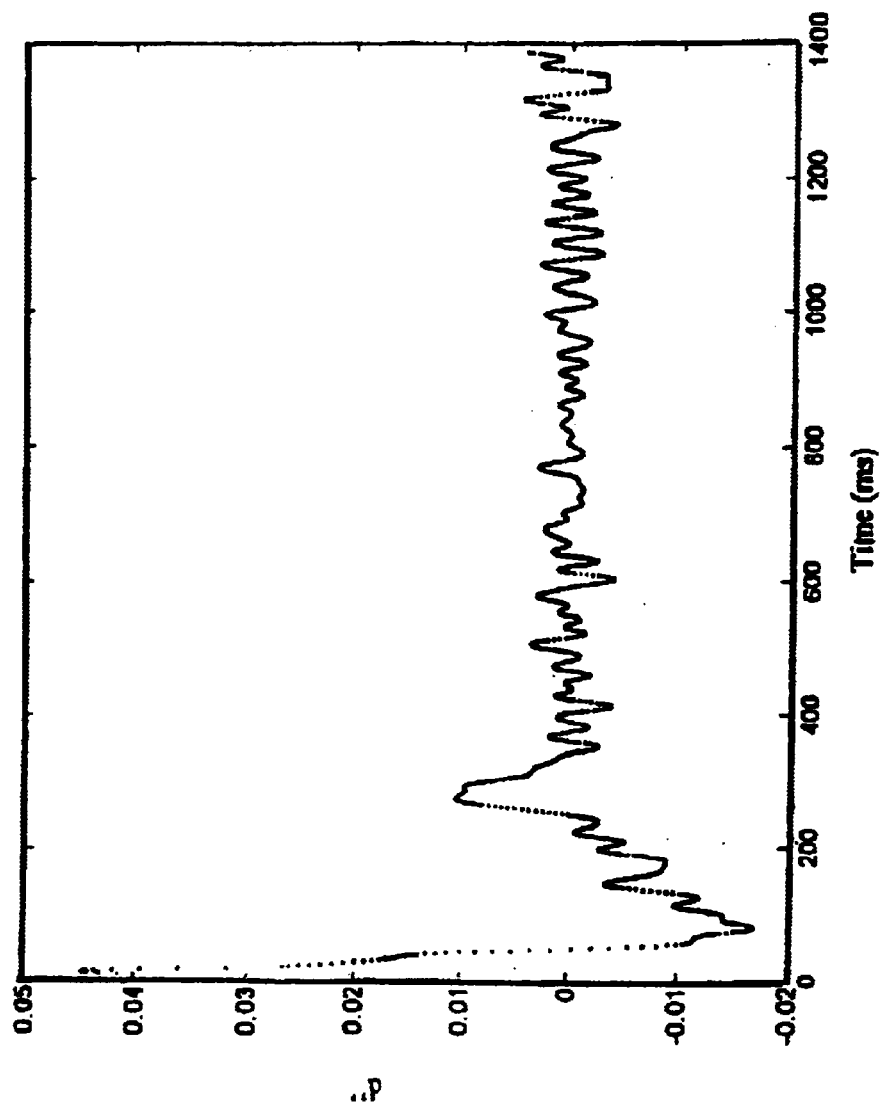

Calculation of RSV when the Pressure is Taken in the Pulmonary Artery (FIG. 7)

EXAMPLE 2A

Mean Pressure in the Pulmonary Artery is Equal or Above 19 mmHG.

In this Example 2A, pressure P(t) is measured in the pulmonary artery and is used to estimate right ventricular stroke volume RSV. This case is very similar to Example 1A above (measurement of aortic pressure), except for the variations in scale of the pressure curve, as can be seen in the exemplary pressure curve shown in FIG. 7. Where Pm>=19, the relationship between RSV and measured points of P(t) should be calculated as follows:

$$RSV = \frac{K}{1000}\left[\frac{A}{(Za1+Za2)*1000} + \frac{A}{(Za1+Za2)*1000} * \frac{(Pm-K1)}{K1}\right] \quad \text{(Equation 3)}$$

where:

K1=19 mmHg (normal physiological pressure in the pulmonary artery)

$Za1=P_{sys}/t_{sys}$ mmHg/ms $Za2=P_{dic}/(t_f-t_{dic})$ mmHg/ms $P_m=(P_{sys}+2^*P_{dia})/3$ The mean pressure value $P_m$ is preferably further adjusted according to the explanation provided in Note 2 below.

FIG. 7 shows acquisition of the pressure signal in the pulmonary artery. For the pressure in pulmonary artery, while not shown in a separate drawing, there are variations for d' and d" similar to those displayed by the signal from the aorta. The determination of the point of dicrotic pressure (Pdic), the systolic pressure (Psys), diastolic pressure (P(1)= Pdia) and the relative times are the same as described above for the case of Example 1A.

Note 2

As in the Example 1, the mean pressure value is preferably further adjusted depending on to what extent $P_m$ deviates from the reference pressure K1, which, in the pulmonary artery, is known to be 19. The calculation of the adjustment must be based on different intervals due to the different pressure ranges. Also, because the absolute pressures are so low, mean pressure and the correction factor is not used at all if Pm<K1, that is, less than 19 mmHg.

The mean pressure in the case of pressure taken in the pulmonary artery must be taken as such and the actual mean pressure value must be used in calculations for the interval of pressure between 19 and 28 mmHg; for values of mean pressure between 28 and 33 mmHg it must be considered at 50%; for values of mean pressure over 33 mmHg it must be considered at 25% (for example, for Pm=43 mmHg, the invention will set an adjusted value of 33 mmHg; for values less than 19 mmHg, mean pressure is preferably not used at all so that adjustment becomes unnecessary.

According to the above, $P_m$ is thus adjusted to a new value $P_m^*$ before being used in the expressions for RSV above as follows:

For $$19<=P_m<=28 \rightarrow P_m^*=P_m$$

$$28<P_m<=33 \rightarrow P_m^*=28+0.5^*(P_m-28)$$

$$P_m>33 \rightarrow P_m^*=30.5+0.25^*(P_m-33)$$

EXAMPLE 2B

Mean Pressure in the Pulmonary Artery is Less Than 19 mmHG

In this case, corresponding to the same conditions as in Example 2A, but with $P_m<19$, no correction factor is used in the calculation of RSV. Thus:

$$RSV = \frac{K}{1000}\left[\frac{A}{(Za1+Za2*1000}\right] \quad \text{(Equation 4)}$$

As before, in both Example 2A and 2B, cardiac output CO=RSV*HR.

EXAMPLE 3

Calculation of LSV when the Pressure is Taken Non-invasively in the Arteriole of the Finger ("f"). (FIGS. 8–19)

EXAMPLE 3A

In this example, the invention is used to determine the cardiac flow in liters per minute by sensing pressure non-invasively, for example, with a finger cuff on the left hand and a sampling frequency of 1000 Hz. This measurement corresponds to the LSV pressure. In this case the pressure curve and its first and second derivatives, d' and d", were of the types as those shown in FIGS. 8, 9 and 10. The calculations were based on the same previously discussed basic formula as follows:

$$LSV = \frac{K}{1000}\left[\frac{A}{(Zf1+Zf2)*1000} + \frac{A}{(Zf1+Zf2)*1000} * \frac{(Pm-K1)}{K1}\right] \quad \text{(Equation 5)}$$

where:

K1=90[mmHg] (normal physiological pressure)
$Zf1=(P_{sys}-P_{dia})/t_{sys}$[mmHg/ms]
$Zf2=P_{dic}/(t_f-t_{dic})$[mmHg/ms]
$P_m=(P_{sys}+2*P_{dia})/3$ The mean pressure value $P_m$ is preferably further adjusted according to the explanation provided in Note 3 below. The rest of the parameters are the same as discussed in relation to FIGS. 1–3. This expression can also be related to Equation C above simply by substituting $Z_{tot}=Zf1+Zf2$ and the values of K1 and $P_m$ given above.

Figure 14:
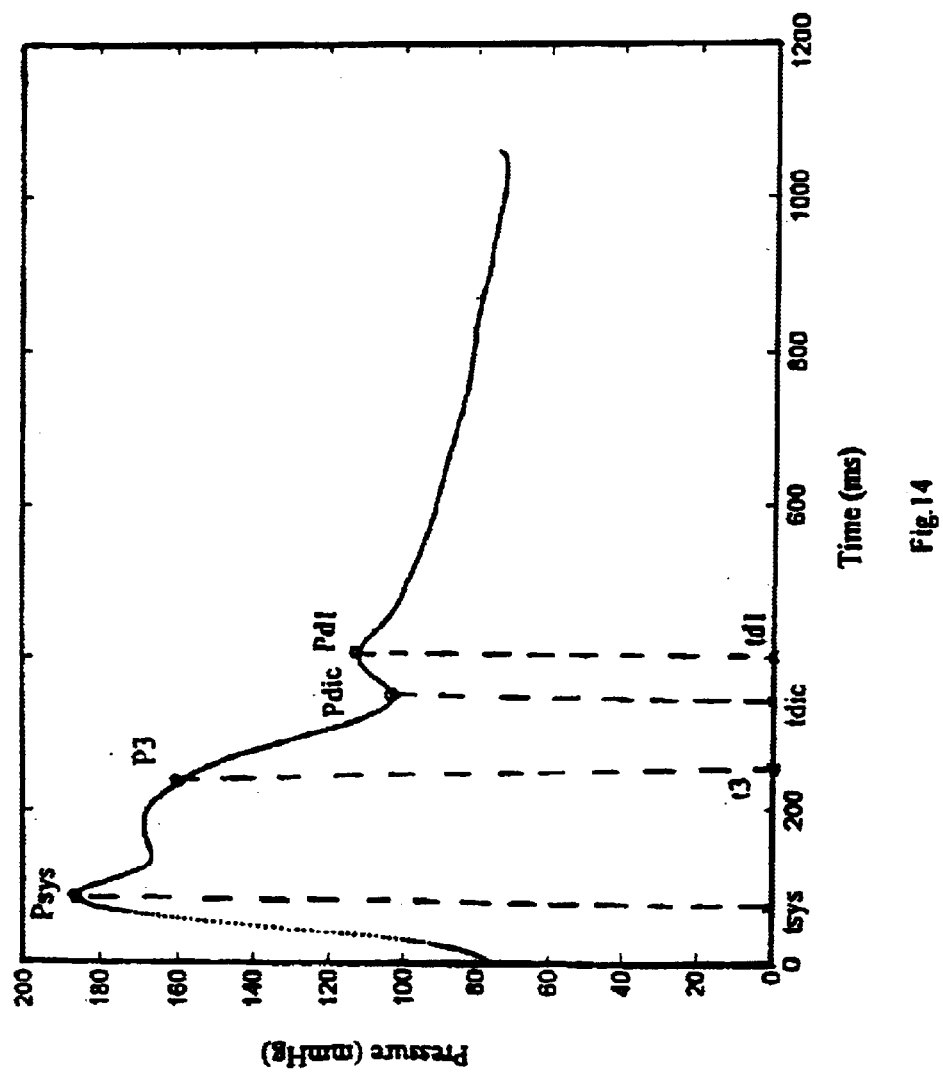

An additional correction may be needed for the volume of blood expelled from the left ventricle (LSVC). This correction is given by the expression $$LSVC = LSV + LSV * \frac{|(Pd1-Pdic)|}{(Psys-Pdia)} \quad \text{(Equation 6)}$$

where (Pd1-Pdic) is the variation in pressure between the dicrotic point (Pdic) and the maximum Pd1 (see FIGS. 11, 14, and 21). Pd1 is the local pressure maximum after the dicrotic point Pdic. This correction is needed only when there is an increase in the pressure after the dicrotic pressure, that is, only when Pd1>Pdic. In the cases in which the increase in pressure is not present, Pd1<Pdic, then no correction is necessary and LSV=LSVC because any correction would be negligible and in any case within the normal range of measurement error.

Cardiac output CO (or, equivalently, flow) in [lit/min] can then be calculated from the expression CO=LSVC*HR.

EXAMPLE 3B

Figure 12:
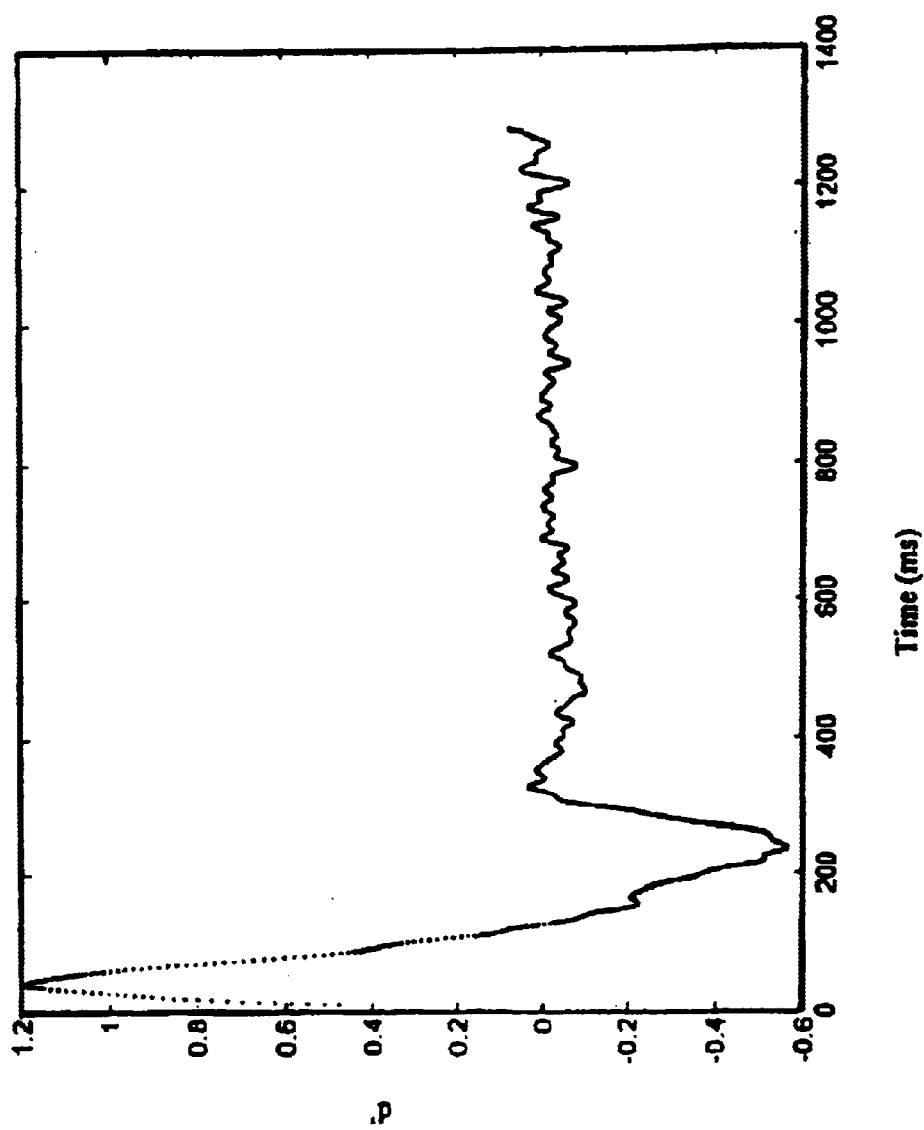
Figure 13:
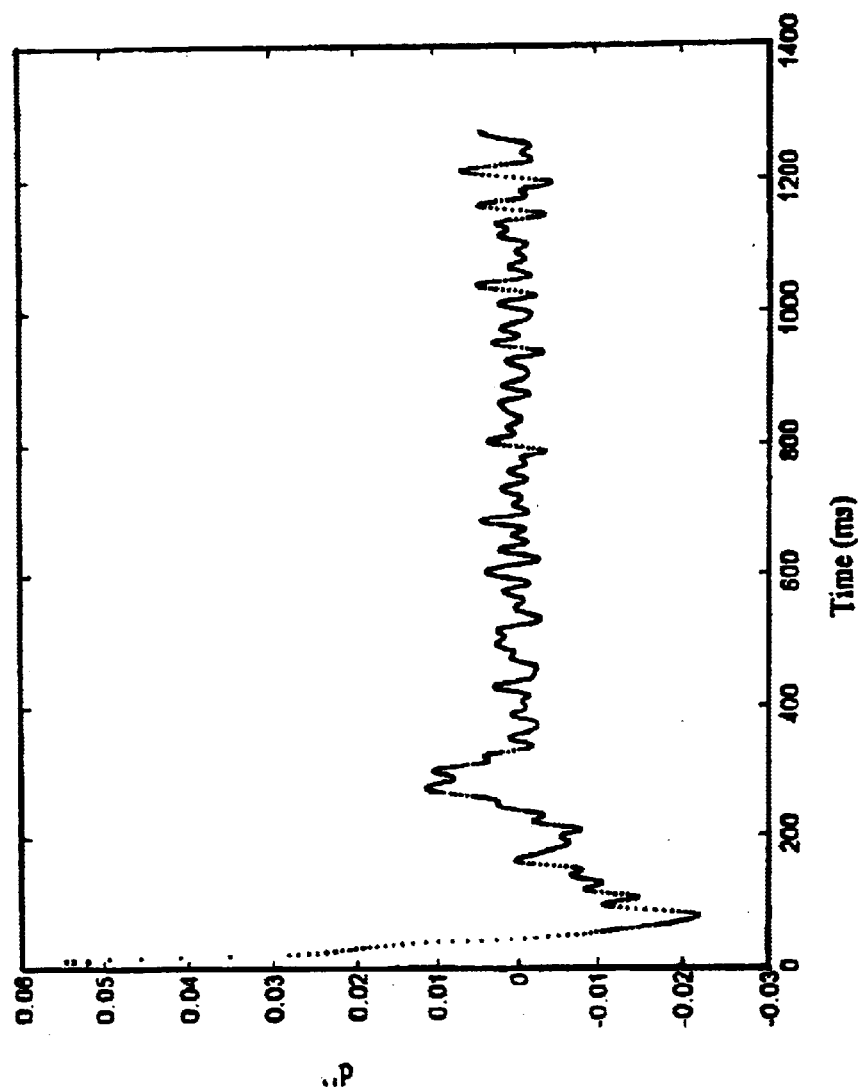

This example is for the case in which the pressure curve displays a relative minimum value of the second derivative of the pressure curve between Psys and Pdic, that is, where P3 has been identified (see FIG. 11), and where the corresponding first and second derivatives, d' and d", of the pressure curves will appear as in FIGS. 12 and 13. The formula for LSV will in this case be:

$$LSV = \frac{K}{1000}\left[\frac{A}{(Zf1+Zf2-Zf3)*1000} + \frac{A}{(Zf1+Zf2-Zf3)*1000} * \frac{(Pm-K1)}{K1}\right] \quad \text{(Equation 7)}$$

where $Zf3=P3/(t_f-t3)$ and other terms and factors are the same as in Example 3A above and t3 is as explained in Example 1B. This expression can also be related to Equation C above simply by substituting $Z_{tot}=Zf1+Zf2-Zf3$ and the values of K1 and $P_m$ given above.

Cardiac output CO can then be calculated from the expression CO=LSVC*HR as before, with the corrected value LSVC being calculated according to the explanation of Example 3A as follows:

$$LSVC = LSV + LSV * \frac{|(Pd1-Pdic)|}{(Psys-Pdia)} \quad \text{(Equation 8)}$$

EXAMPLE 3C

Figure 15:
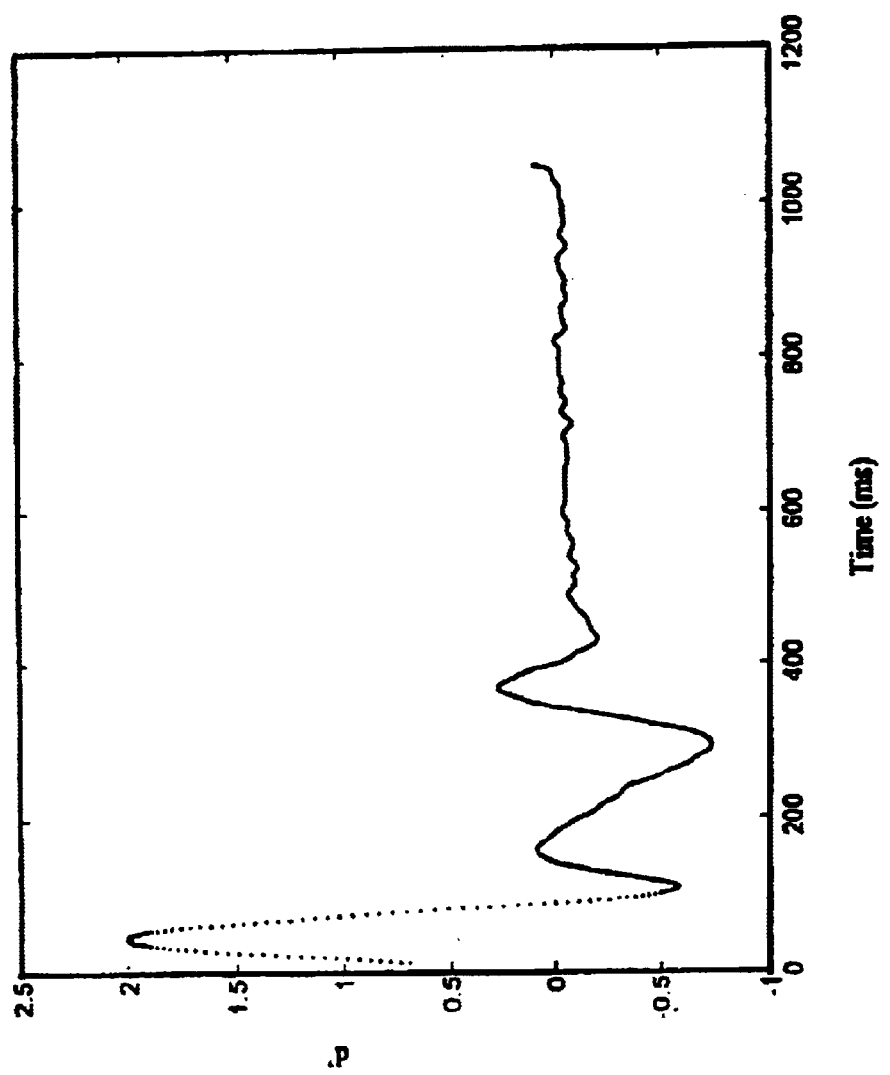
Figure 16:
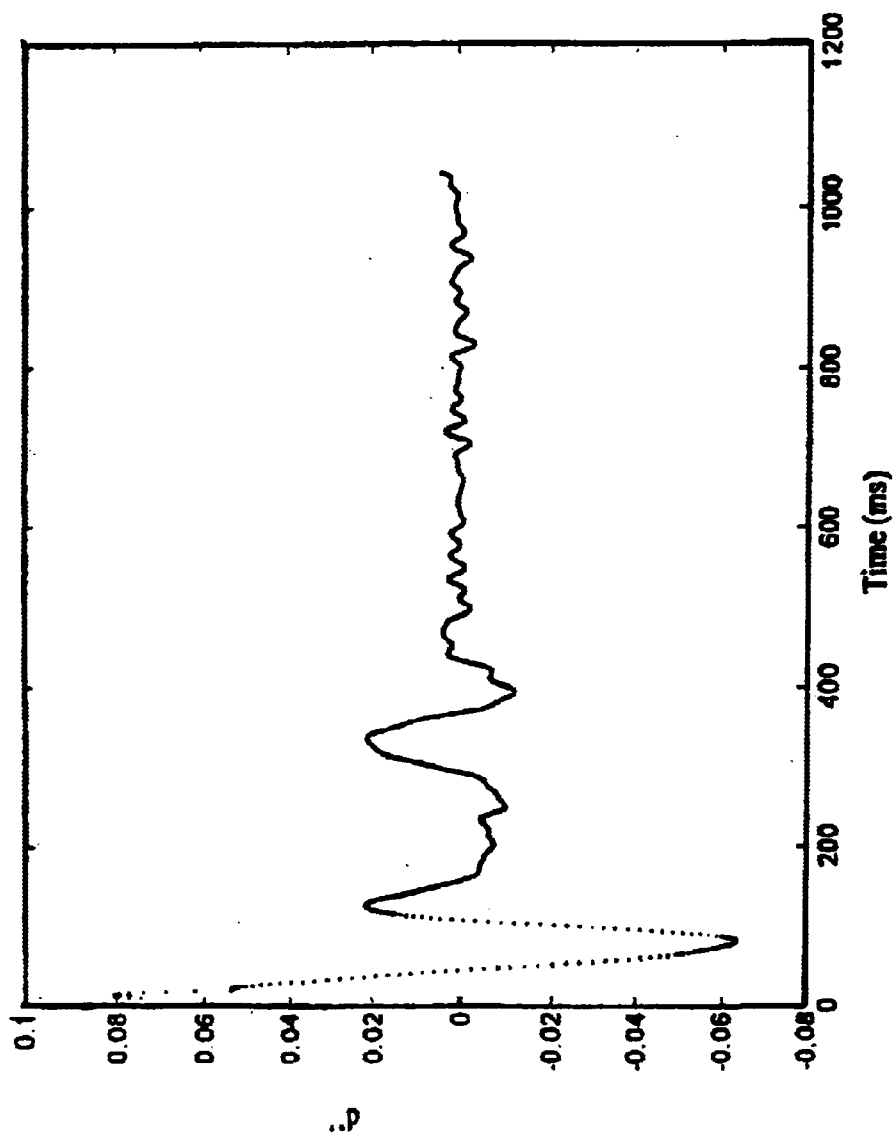

This example is for the case in which the pressure curve is as shown in FIGS. 14 and 21, with first and second derivatives, d' and d", as in FIGS. 15 and 16, respectively. Note that, in this case, there is a detectable local minimum between systolic peak at Psys and the dicrotic notch at Pdic as can be seen in FIG. 14 and as is specifically marked $P_{lmin}$ in FIG. 21. The formula for LSV will in this case be:

$$LSV = \frac{K}{1000}\left[\frac{A}{(Zf1+Zf2-2*Zf3)*1000} + \frac{A}{(Zf1+Zf2-2*Zf3)*1000} * \frac{(Pm-K1)}{K1}\right] \quad \text{(Equation 9)}$$

Note that although $Zf3=P3/(t_f-t3)$ as in Example 3B, this term is multiplied by two in this expression. As all others, this expression can be related to Equation C above simply by substituting $Z_{tot}=Zf1+Zf2-2*Zf3$ and the values of K1 and $P_m$ given above in the Examples 3A and 3B.

Cardiac output CO can then be calculated as in Example 3A from the expression CO=LSVC*HR, where:

$$LSVC = LSV + LSV * \frac{|(Pd1-Pdic)|}{(Psys-Pdia)} \quad \text{(Equation 10)}$$

EXAMPLE 3D

Figure 17:
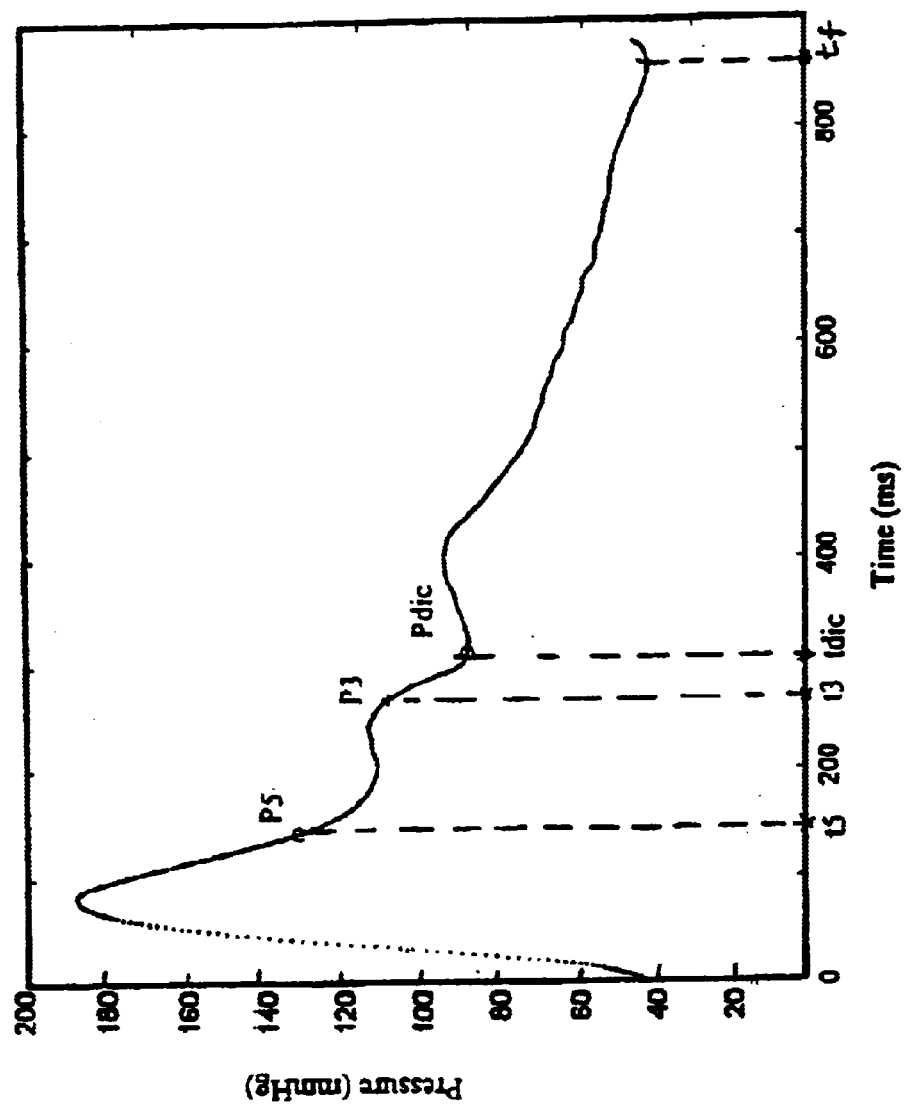
Figure 18:
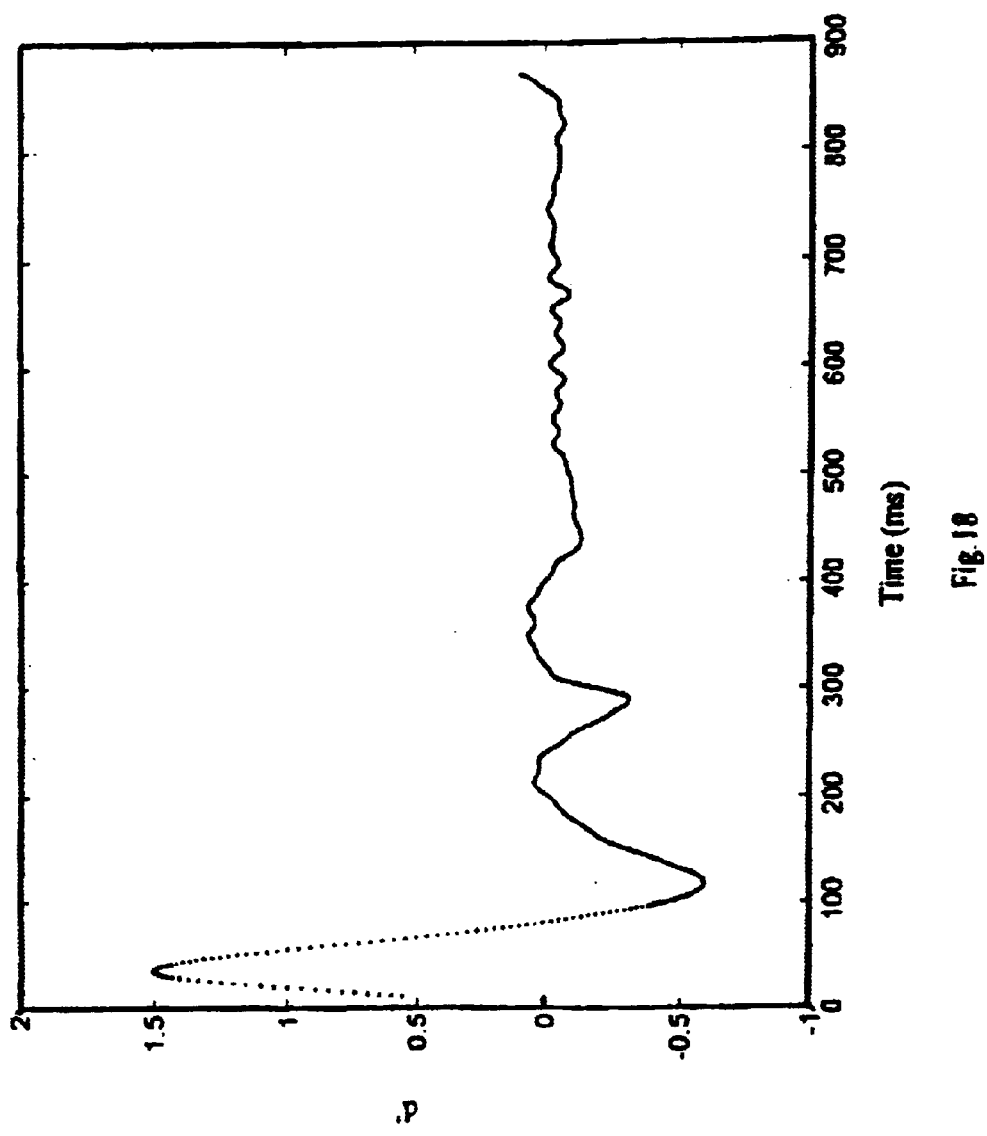
Figure 19:
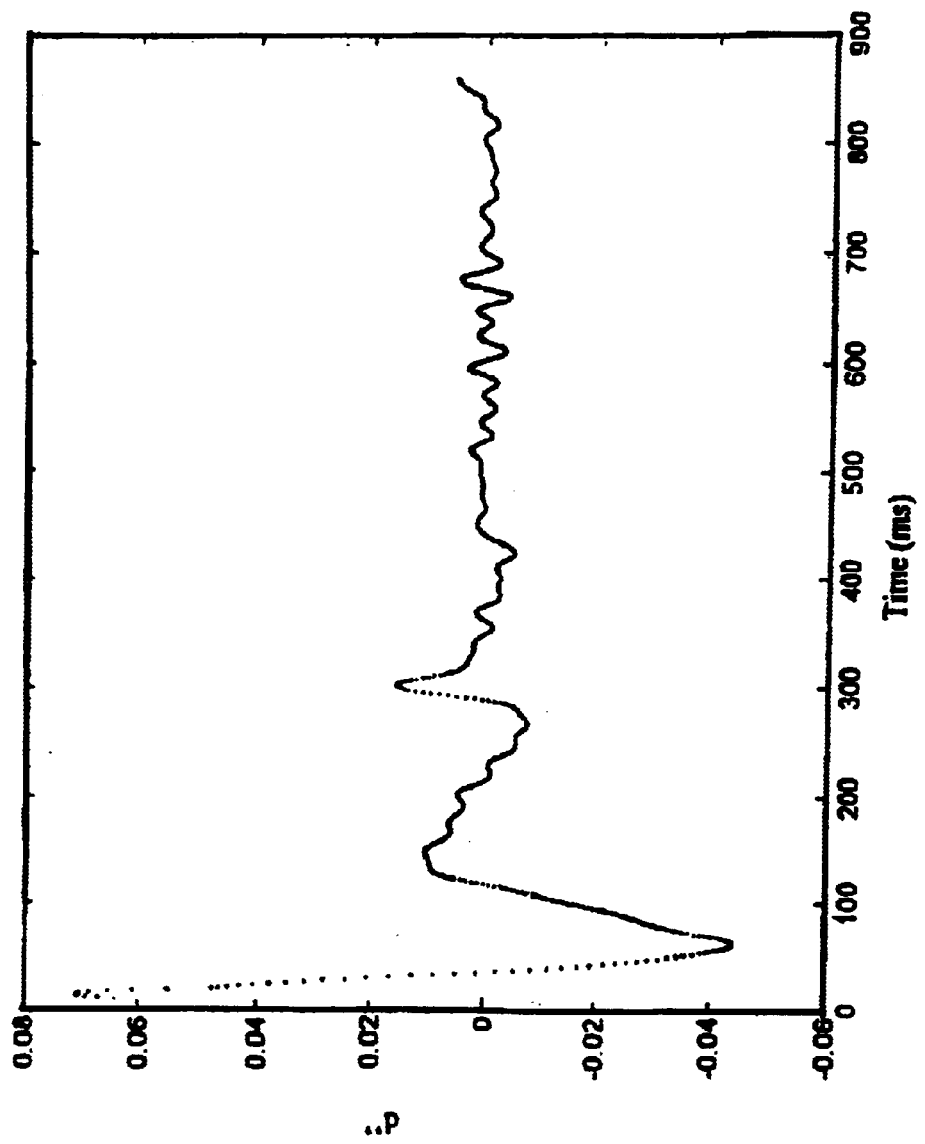

FIG. 17 illustrates a pressure curve that has two resonance or balancing points P3 and P5 between the systolic peak and the dicrotic notch, as well as the local minimum as in FIG. 14 (and Example 3A). The resonance points P3 and P5 represent the balance between the perturbative terms and the fundamental contribution that generates the main pressure wave. The resonance points are therefore points at which the system of forces is in equilibrium. This is also illustrated in FIG. 21. FIGS. 18–19 show the corresponding first and second derivatives, d' and d." Thus, the second derivative d" of the pressure curve is at its minimum at point P3 at time t3 and at its maximum of second derivative (after Psys) at P5 at time t5.

Here, the formula used for Example 3C is further modified as follows:

$$LSV = \frac{K}{1000}\left[\frac{A}{(Zf1+Zf2-2*Zf3-Zf5)*1000} + \frac{A}{(Zf1+Zf2-2*Zf3-Zf5)*1000} * \frac{(Pm-K1)}{K1}\right] \quad \text{(Equation 11)}$$

where:

$Zf3 = P3/(t_f-t3)$ $Zf5 = P5/(t_f-t5)$

All symbols have the same meaning as previously explained, and t5 is the time (expressed in [ms]) of the maximum of the second derivative d" between the time $t_{sys}$ and the time $t_{dic}$ while P5 is the corresponding pressure in [ms] at time t5.

Of course, this expression also corresponds to Equation C, with $Z_{tot} = Zf1+Zf2-2*Zf3-Zf5$.

Cardiac output CO can then be calculated from the expression CO=LSVC*HR, where:

$$LSVC = LSV + LSV * \frac{|(Pdia - Pdic)|}{(Psys - Pdia)}$$

Note 3

Examples 3A–3D all involve non-invasive determination of cardiac output. As in earlier examples, the value of mean pressure Pm is preferably adjusted. The mean pressure in the case of the pressure taken at the arterial finger non-invasively must be considered as such and the actual value must be used for the interval of mean pressure $P_m$ between 70 and 110 mmHg, which represents a 40 mmHg interval centered on the reference pressure K1=90 mmHg. For the values of mean pressure between 110 and 140 and between 70 and 40 mmHg it must be considered at 50% (for example a raw Pm value of 128 will be adjusted to 119 mmHg); for mean values of pressure greater than 140 or less that 40 mmHg, mean pressure is considered at 25%.

$P_m$ is thus adjusted to a new value $P_{m*}$ as follows before being used in the expressions for LSV above:

For $P_m > 140 {:} \rightarrow P_m^* = 120 + 0.25*(P_m - 140)$ $110 < P_m <= 140 \rightarrow P_m^* = 110 + 0.5*(P_m - 110)$ $70 < P_m <= 110 {:} \rightarrow P_m^* = P_m$ $40 < P_m <= 70 \rightarrow P_m^* = 70 + 0.5*(P_m - 70)$ $P_m <= 40 \rightarrow P_m^* = 40 + 0.25*(P_m - 40)$ Examples 3A–3D relate primarily to the case of non-invasive sensing of pressure. The expressions used in those examples may, however, in some cases provide accurate results even when used in implementations in which pressure is sensed invasively, such as in the aorta. It will only require the use of K1 corresponding to the aorta, or other actual location.

EXAMPLE 4

Calculation of SV when the Pressure is Taken in the Radial, Femoral, Brachial or Other Peripheral Artery The invention may also be used to determine the relationship between LSV and the pressure recorded invasively from femoral artery or from another peripheral point such as brachial or radial artery. In this case of Example 4 it has been discovered that all formulae, including corrections and adjustments, used for Examples 3A–3D may also be used, with the modification that K1 for these moderately or less invasive signals should be set in a range from 90 to 100 mmHg depending on the location and size of the peripheral artery.

Reconstruction of Aortic Pressure Signal

Figure 20:
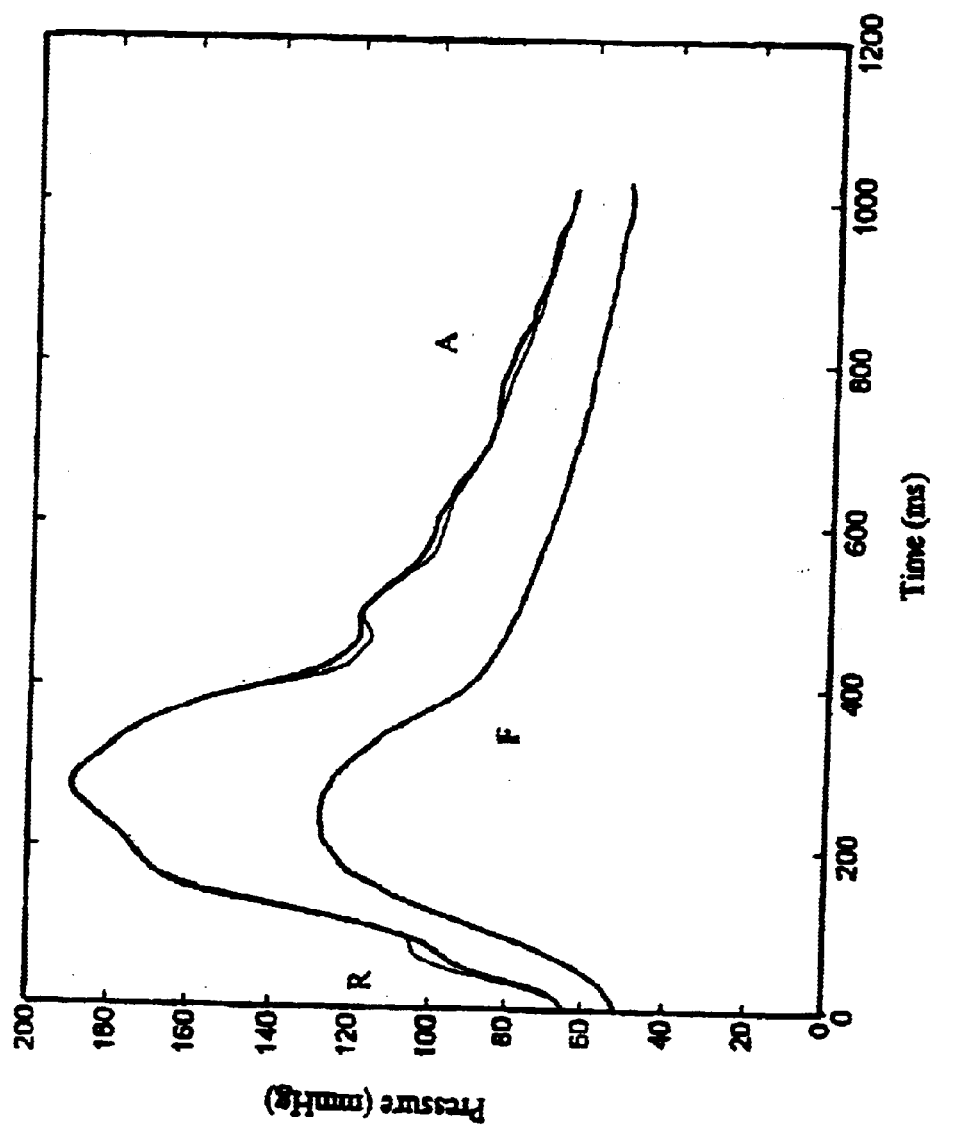
FIG. 20 shows a reconstruction of a pressure signal in the aorta of a patient based on parameters extracted from a pressure signal taken at the arteriole of a finger using the method according to the invention.

FIG. 20 illustrates the results of reconstructing the pressure signal, for example, in the ascending aorta (or, if desired, in the pulmonary artery) based on the terms Zf1–Zf5, which were derived as described above in Example 3 according to the present invention from a pressure signal sensed using a non-invasive finger pressure sensor, mounted on a small cuff wrapped around the middle finger of the left hand. The pressure curve identified with a letter "F" in FIG. 20 is a finger pressure curve while the pressure curve identified with a letter "A" shows aortic pressure recorded in the aortic root, and the curve identified with the letter "R" shows the aortic signal pressure as reconstructed from the measured finger pressure. In order to reconstruct the signal, a linear multiple regression was used.

The reconstructed pressure signal was obtained in two successive steps. First, an estimate was made of the mean pressure during the cardiac cycle in the ascending aorta (or in the pulmonary artery) using the signal taken at the finger, which gave the value Pm as described in the above formulas and the various examples of the invention. The parameters Zf1–Zf5 were then determined in the manner described above. A best-fit curve was then reconstructed using multiple linear regression based on the parameters Zf1–Zf5. The general principles of multiple linear regression were applied using the formulae of the present invention and in the context of the present invention.

The reconstructed signal was then compared with an invasively determined pressure profile measured in the ascending aorta (or in the pulmonary artery). As FIG. 20 illustrates, the reconstructed pressure curve ("R") closely approximates the curve obtained using a conventional, highly invasive technique ("A"), which indicates that the parameters measured according to the invention contain information sufficient to accurately characterize the pressure curve. The exemplary errors in the comparison between the reconstructed curve of the signal registered non-invasively and that taken directly near the ascending aorta are as follows:

| SD (mmHg) | Max (mmHg) | Min (mmHg) |
|---|---|---|
| 1.16 ÷ 5.67 | 2.38 ÷ 16.40 | −2.82 ÷ 16.41 |
| mean 3.41 | 9.37 | −9.32 |

With SD=Standard Deviation: the minimum of the interval is obtained for the reconstruction of the points around the diastolic pressure, the maximum of the difference is obtained near the point of the systolic pressure.

Max=interval of overestimation of the pressure in the point taken into consideration reconstructed and that actually measured with the catheter during the cardiac beat. The minimum of this interval is obtained for the reconstruction of the points around the diastolic pressure, the maximum of the difference is obtained near the points of systolic pressure.

Min=interval of underestimation of the pressure in the point taken into consideration reconstructed and that is actually measured with the catheter during the cardiac beat.

The minimum of this interval is obtained for the reconstruction of the points around the diastolic pressure, the maximum of the difference is obtained near the points of systolic pressure.

The reconstruction shows that the present invention provides very satisfactory results since it does not discard information that the prior art ignores, such as the information contained in the continuous, non-pulsatile portion of the pressure curve, including the information in the pressure curve after the dicrotic notch, that is, between the dicrotic notch and the end of the cardiac cycle.

System Components

Figure 22:
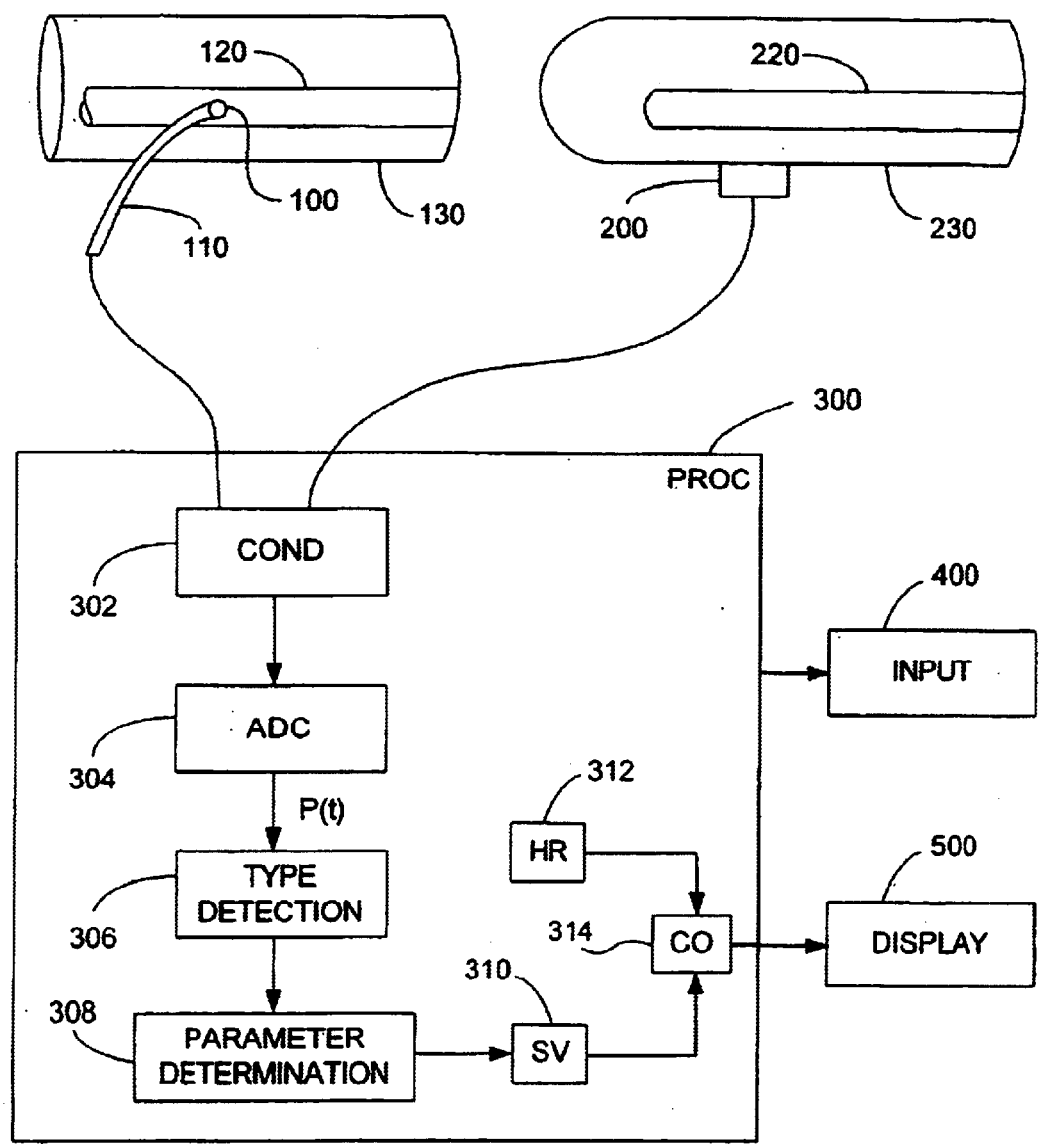
FIG. 22 is a block diagram showing the main components of a system according to the invention.

FIG. 22 shows the main components of a system according to the invention for sensing pressure and calculating CO. As is mentioned above, pressure may be sensed in either or, indeed, both, of two ways: invasively and non-invasively. FIG. 22 shows both types of pressure sensing for the sake of conciseness; in most practical applications of the invention, either one or several variations will typically be implemented.

In the invasive applications of the invention, a conventional pressure sensor 100 is mounted on a catheter 110, which is inserted in an artery 120 of a portion 130 of a patient's body. Such artery could be an ascending aorta, or pulmonary artery, or, in order to reduce the level of invasiveness, the artery 120 could be peripheral, such as the femoral, radial or brachial artery. In the non-invasive applications of the invention, a conventional pressure sensor 200, such as a photo-plethysmographic blood pressure probe, is mounted externally in any conventional manner, for example using a cuff, for example, around a finger 230 of a patient. FIG. 22 schematically shows both types.

The signals from the sensors 100, 200 are passed via any known connectors as inputs to a processing system 300, which includes one or more processors and other supporting hardware and system software (not shown) usually included to process signals and execute code. In this invention, however, the processing system 300 also may include, or is connected to, conditioning circuitry 302 which performs such normal signal processing tasks as amplification, filtering, ranging, etc,. as needed. The conditioned, sensed input pressure signal is then converted to digital form by a conventional analog-to-digital converter ADC 304. As is well understood, the sampling frequency of the ADC 304 should be chosen with regard to the Nyquist criterion so as to avoid aliasing of the pressure signal; this procedure is very well known in the art of digital signal processing.

The output from the ADC 304 will be the pressure signal P(t), whose values may be stored in conventional memory circuitry (not shown). A type detection software module 306 is preferably included in order to analyze the pressure signal P(t) with respect to the various factors described above, in particular the derivatives of P(t), the presence of one or more local minima, etc. This analysis will then indicate which type of pressure curve is present, and thus which formula is to be used for evaluation of LSV or RSV as the case may be. This module 306 may of course be omitted in cases where it is known which type of pressure source, for example a finger, is always to be used.

A software module 308 is also included to analyze the pressure curve P(t) and determine the values of the parameters used in the CO calculations described above. These parameters may include any of the following: A, the various components of $Z_{tot}$, the mean pressure $P_m$, etc. Note that, if appropriate, some parameters may be fixed parameters, or may be input by a user, for example, via any standard input device 400. For example, a location of the pressure sensor (such as an aorta, or a pulmonary artery, or a radial artery) may be input by a user.

The parameter values calculated by the module 308 are then passed as inputs to a subsequent software module 310 that evaluates the appropriate expression for SV (LSV or RSV). The patient's current heart rate HR is either calculated from the pressure curve or is otherwise measured by a software module 312 or conventional hardware device. The heart rate HR and the computed values of SV are then passed as inputs to a software routine 314 that multiplies these values to provide a value of cardiac output. This CO value may then be output to any conventional display or printing device 500 for the user to view and monitor.

The invention further relates to a computer program loadable in a computer unit or processing system 300 in order to execute the method of the invention. Moreover, the various software modules 304, 306, 308, 310, 312, 314 used to perform the various calculations and perform related method steps according to the invention may also be stored as computer-executable instructions on a computer-readable medium in order to allow the invention to be loaded into and executed by different processing systems 300.

Although not required, if desired the method according to the invention may also be used in combination with known methods (such as the thermodilution method) comprising a phase of calibration of the recorded pressure signal. Using such known methods, the contribution of the area under the pressure curve is considered variable over time, whereas the contribution of the impedance is considered constant. In such a combined application, the method according to the invention also makes it possible to take into account even major variations in the heart rate, in the pressure values and in the pressure waveform for purposes of calculation of the impedance.

Main Advantages of the Invention

From the description of the invention above one should understand that, both in the case of normal subjects and in the case of patients affected by various pathological conditions, the method according to the invention represents an effective and advantageous diagnostic tool in both the invasive and non-invasive evaluation of cardiac flow. In addition, the method can be applied both in healthy subjects and in subjects presenting cardiocirculatory alterations who are undergoing ergometric tests that are aimed at establishing the level of haemodynamic response to the tests.

One advantage of the invention is that it relies solely only on analysis of the pressure signal (recorded invasively in the pulmonary artery and in the aortic arch, or in any other major arterial vessel, or non-invasively, for example, at the finger), and is independent of the anthropometric data, including such patient-specific parameters as weight, height, body surface area, sex, age, the diameter of the aorta of the patient, etc. Moreover, the invention is able to accurately measure cardiac output with no need for prior calibration. Furthermore, the invention determines impedance values that are specific to each patient under study and does not simply rely on standard values or values derived from measurements taken from several patients.

The invention was developed based on the theory of the perturbations, which takes into account the ever-changing relative weight of the several physical variables involved in the continuous transmission of the pressure wave. The invention therefore considers the contributions of a plurality of forces in order to evaluate the influence even of the interdependent components of the forces that are not directly involved in the main interaction.

As is mentioned above, the method according to the invention uses, to calculate the value A, the entire area under the pressure curve, not just the pulsatile component that lies above the diastolic baseline, that is, above the horizontal line at P(t)=Pdia. This allows the method according to the invention to be used even in the case of an extracorporeal circulation, when the pulsatile component of the pressure curve is substantially negligible and the prior art methods cannot work at all As is demonstrated by the discussion of the various examples of the invention and as demonstrated in FIGS. 1–19 of the pressure curve, the parameters included in the calculations according to the invention contain information about the entire pressure curve, including its derivatives, not just the portion up to the dicrotic notch or just above the $P_{dia}$. In the calculation of both $Z_{tot}$ and A, the invention considers the contribution of two phases: pulsatile and continuous. In calculation of A, the continuous phase is considered, as shown in FIG. 1, by including the area below the $P_{dia}$. In calculations of $Z_{tot}$, the pulsatile phase is mainly reflected, for example, by a component Zf1 while the continuous phase is reflected mainly by the components Zf2, Zf3 or Zf5, as may be appropriate, in each particular embodiment. Consequently, the invention takes into account values of the pressure curve not just within the systolic phase, but also within the diastolic phase, and importantly, includes the continuous component. The invention is thus better able to account for irregularities of the heart beat occurring during the diastolic pulse, which modify the cardiac flow output.

What is claimed is:

1. A method for measuring cardiac output (CO) of a patient, comprising the following steps: sensing arterial blood pressure and converting the sensed arterial blood pressure to a pressure signal; calculating an estimate of stroke volume as a function only of selected characteristics of the sensed pressure signal, including calculating an area (A) under the entire pressure signal including both pulsatile and non-pulsatile portions of the pressure signal; and calculating an estimate of CO as a function of the estimated stroke volume and a current heart rate value.

2. A method as in claim 1, in which the step of calculating the estimate of stroke volume comprises the following sub-steps: estimating selected impedance values from the pressure signal; and calculating the estimate of stroke volume as a function of a ratio between the calculated area and the estimated selected impedance values.

3. A method as in claim 1, in which the step of calculating the estimate of stroke volume further comprises the following sub-steps:

calculating a mean pressure value of the pressure signal; and correcting the estimated stroke volume as a predetermined function of the mean pressure value and of a reference pressure.

4. A method as in claim 1, further including the following steps:

detecting times and corresponding pressure values of a systolic peak and of a dicrotic notch in the pressure signal;

evaluating a second derivative of the pressure signal between the systolic peak and the dicrotic notch;

detecting the time and corresponding pressure value of at least one intermediate point in the pressure signal between the systolic peak and the dicrotic notch at which the second derivative has an extreme value; and estimating at least one of the selected impedance values as a predetermined function of the time and corresponding pressure value of the intermediate point.

5. A method as in claim 1, further including the following steps: detecting a systolic peak pressure Psys, a diastolic pressure Pdia, and a dicrotic pressure Pdic; and scaling the estimated stroke volume by a factor proportional to the ratio between the difference between Pdia and Pdic and the difference between Psys and Pdia.

6. A method as in claim 1, further including the following steps:

detecting a dicrotic time in the pressure signal;

evaluating a post-dicrotic first derivative of a post-dicrotic portion of the pressure signal at times after the dicrotic time;

detecting the time and corresponding pressure value of at least one local maximum pressure in the post-dicrotic portion of the pressure signal; and estimating at least one of the selected impedance values as a predetermined function of the time and corresponding pressure value of the local maximum pressure.

7. A method as in claim 1, in which the step of calculating the CO estimate is performed based on the pressure signal during a single cardiac cycle.

8. A method as in claim 1, in which the pressure signal is uncalibrated, whereby the steps of calculating the estimate of the stroke volume and calculating the estimate of CO are independent of external calibration.

9. A method as in claim 1, in which the arterial blood pressure is sensed non-invasively using an externally mounted sensor.

10. A method as in claim 9, in which the arterial blood pressure is sensed using a finger-mounted pressure sensor.

11. A method as in claim 1, in which the step of sensing arterial blood pressure comprises inserting a catheter-mounted pressure sensor into an artery of the patient.

12. A method as in claim 11, in which the artery is the radial artery of the patient.

13. A method as in claim 11, in which the artery is the pulmonary artery of the patient.

14. A method as in claim 11, in which the artery is the femoral artery of the patient.

15. A method as in claim 11, in which the artery is the aortic artery of the patient.

16. A method as in claim 11, in which the artery is the aortic artery of the patient.

17. A method as in claim 1, further comprising the step of generating at least one calibrated impedance value using a thermodilution method before calculating the estimate of stroke volume.

18. A method for measuring cardiac output (CO) of a patient comprising the following steps: sensing arterial blood pressure and converting the sensed arterial blood pressure to a pressure signal; calculating area under the entire pressure signal including both pulsatile and non-pulsatile portions of the pressure signal, over a cardiac cycle; estimating selected impedance values from the pressure signal calculating a mean pressure value of the pressure signal; calculating a mean pressure value of the pressure signal; calculating an estimate of stroke volume as function only of selected characteristics of the sensed pressure signal and of predetermined constants, including, the selected characteristics including the ratio between the calculated area and the estimated selected impedance values; and calculating an estimate of CO as a function of the corrected, estimated stroke volume and a current heart rate value; in which the pressure signal is uncalibrated, whereby the steps of calculating the estimate of the stroke volume of calculating the estimate of CO are independent of external calibration.

19. A method as in claim 18, further including the following steps: detecting times and corresponding pressure values of a systolic peak and of a dicrotic notch in the pressure signal; evaluating a second derivative of the pressure signal between the systolic peak and the dicrotic notch; detecting the time and corresponding pressure value of at least one intermediate point in the pressure signal between the systolic peak and the dicrotic notch at which the second derivative has an extreme value; and estimating at least one of the selected impedance values as a predetermined function of the time and corresponding pressure value of the intermediate point.

20. A method as in claim 18, further including the following steps: detecting a systolic peak pressure Psys, a diastolic pressure Pdia, and a dicrotic pressure Pdic; and scaling the estimated stoke volume by a factor proportional to the ratio between the difference between Pdia and Pdic and the difference between Psys and Pdia.

21. A system for measuring cardiac output (CO) of a patient, which does not require calibration, comprising:
pressure sensing means for sensing arterial blood pressure;
signal processing means for converting the sensed arterial blood pressure to a pressure signal;
processing means for calculating an estimate of stroke volume as a function only of selected characteristics of the sensed pressure signal, including calculating an area (A) under the entire pressure signal including both pulsatile and non-pulsatile portions of the pressure signal, over a cardiac cycle, and for calculating an estimate of CO as a function of the estimated stroke volume and a current heart rate value.

22. A system as in claim 21, in which the pressure sensing means is non-invasive and externally mounted on the patient.

23. A system as in claim 21, in which the pressure sensing means is a finger-mounted pressure sensor.

24. A system as in claim 21, in which the pressure sensing means is an intra-arterial, catheter-mounted pressure sensor.

25. A computer-readable medium having computer-executable instructions for performing steps for measuring cardiac output (CO) of a patient comprising the following steps:
sensing arterial blood pressure and converting the sensed arterial blood pressure to a pressure signal;
calculating an estimate of stroke volume as a function only of selected characteristics of the sensed pressure signal, including calculating an area (A) under the entire pressure signal including both pulsatile and non-pulsatile portions of the pressure signal, over a cardiac cycle; and
calculating and outputting an estimate of CO as a function of the estimated stroke volume and a current heart rate value.

26. A method for measuring cardiac output (CO) of a patient, comprising the following steps: sensing arterial blood pressure and converting the sensed arterial blood pressure to a pressure signal; calculating an estimate of stroke volume as a function only of selected characteristics of the sensed pressure signal; and calculating an estimate of CO as a function of the estimated stroke volume and a current heart rate value; wherein the method does not require calibration.

27. A method for measuring cardiac output (CO) of a patient, comprising the following steps: sensing arterial blood pressure and converting the sensed arterial blood pressure to a pressure signal; calculating an estimate of stroke volume as a function only of selected characteristics of the sensed pressure signal, including a time value and a corresponding pressure value at a selected point of the pressure signal; and calculating an estimate of CO as a function of the estimated stroke volume and a current heart rate value.

28. A method as in claim 27, further comprising the step of generating at least one calibrated impedance value using a thermodilution method before calculating the estimate of stroke volume.

29. A system for measuring cardiac output (CO) of a patient, comprising:
pressure sensing means for sensing arterial blood pressure;
signal processing means for converting the sensed arterial blood pressure to pressure to a pressure signal;
processing means for calculating an estimate of stroke volume as a function only of selected characteristics of the sensed pressure signal, and for calculating an estimate of CO as a function of the estimated stroke volume and a current heart rate value;
wherein the system is constructed and arranged to perform the calculation of estimated CO without calibration.

30. A system for measuring cardiac output (CO) of a patient, comprising:
pressure sensing means for sensing arterial blood pressure;
signal processing means for converting the sensed arterial blood pressure to a pressure signal;
processing means for calculating an estimate of stroke volume as a function only of selected characteristics of the sensed pressure signal, including a time value and a corresponding pressure value at a selected point of the pressure signal, and for calculating an estimate of CO as a function of the estimated stroke volume and a current heart rate value.

31. A computer-readable medium having computer-executable instructions for performing steps for measuring cardiac output (CO) of a patient comprising the following steps:
sensing arterial blood pressure and converting the sensed arterial blood pressure to a pressure signal;
calculating an estimate of stroke volume as a function only of selected characteristics of the sensed pressure signal; and
calculating and outputting an estimate of CO as a function of the estimated stroke volume and a current heart rate value without using a calibration value.

32. A computer-readable medium having computer-executable instructions for performing steps for measuring cardiac output (CO) of a patient comprising the following steps:
sensing arterial blood pressure and converting the sensed arterial blood pressure to a pressure signal;
calculating an estimate of stroke volume as a function only of selected characteristics of the sensed pressure signal, including a time value and a corresponding pressure value at a selected point of the pressure signal; and
calculating and outputting an estimate of CO as a function of the estimated stroke volume and a current heart rate value.

* * * * *